(12) United States Patent
Tomasello

(10) Patent No.: US 8,663,210 B2
(45) Date of Patent: Mar. 4, 2014

(54) METHODS AND APPARATUS FOR PERFORMING INTERSTITIAL LASER THERAPY AND INTERSTITIAL BRACHYTHERAPY

(75) Inventor: Anthony J. Tomasello, Sewickley Heights, PA (US)

(73) Assignee: Novian Health, Inc., Chicago, IL (US)

( * ) Notice: Subject to any disclaimer, the term of this patent is extended or adjusted under 35 U.S.C. 154(b) by 300 days.

(21) Appl. No.: 12/778,580

(22) Filed: May 12, 2010

(65) Prior Publication Data

US 2010/0292682 A1 Nov. 18, 2010

Related U.S. Application Data

(60) Provisional application No. 61/177,861, filed on May 13, 2009.

(51) Int. Cl.
*A61B 18/18* (2006.01)
*A61N 5/10* (2006.01)
*G21K 1/00* (2006.01)

(52) U.S. Cl.
USPC ......... 606/15; 606/11; 378/65; 378/145

(58) Field of Classification Search
USPC ......... 606/7, 10–13, 15–19; 378/65, 145, 210
See application file for complete search history.

(56) References Cited

U.S. PATENT DOCUMENTS

| | | |
|---|---|---|
| 4,190,461 A | 2/1980 | Hedger |
| 4,510,924 A | 4/1985 | Gray |
| 4,763,671 A | 8/1988 | Goffinet |
| 4,815,449 A | 3/1989 | Horowitz |
| 4,976,680 A | 12/1990 | Hayman et al. |
| 5,084,001 A | 1/1992 | Van't Hooft et al. |
| 5,141,487 A | 8/1992 | Liprie |
| 5,153,900 A | 10/1992 | Nomikos et al. |
| 5,169,396 A | 12/1992 | Dowlatshahi et al. |
| 5,222,953 A | 6/1993 | Dowlatshahi |
| 5,339,812 A | 8/1994 | Hardy et al. |
| 5,411,477 A * | 5/1995 | Saab ........................ 604/103.13 |

(Continued)

OTHER PUBLICATIONS

A fibre optic scintillator dosimeter for absorbed dose measurements of low-energy X-ray-emitting brachytherapy sources, Sliski, Alan et al., Radiation Protection Dosimetry, Jun. 16, 2006.

(Continued)

*Primary Examiner* — Dawayne A Pinkney
(74) *Attorney, Agent, or Firm* — Neal, Gerber & Eisenberg LLP

(57) ABSTRACT

A therapeutic energy system for performing interstitial laser therapy and brachytherapy includes two categories of components. The first category includes components usable to perform both interstitial laser therapy and brachytherapy. The second category of components includes components usable to perform either interstitial laser therapy or brachytherapy, but not both. The components co-act to apply therapeutic energy to tissue. The components of the first system include components inserted percutaneously into the tissue, such that interstitial laser therapy and brachytherapy can be performed sequentially without removing and re-inserting percutaneous components. Components of the second category include components not requiring additional puncturing of the skin of a patient, such that removing and inserting components of the second category from a patient is done easily and painlessly. An energy probe component does not maintain a cavity around the tumor mass. Surgical excision of tissue can be performed coincident to therapeutic energy treatment as disclosed.

12 Claims, 8 Drawing Sheets

(56) References Cited

U.S. PATENT DOCUMENTS

| | | |
|---|---|---|
| 5,428,658 A | 6/1995 | Oettinger et al. |
| 5,429,582 A | 7/1995 | Williams |
| 5,569,240 A | 10/1996 | Dowlatshahi et al. |
| 5,695,479 A | 12/1997 | Jagpal |
| 5,713,828 A | 2/1998 | Coniglione |
| 5,807,395 A | 9/1998 | Mulier et al. |
| 5,853,366 A | 12/1998 | Dowlatshahi |
| 5,868,757 A | 2/1999 | Koutrouvelis |
| 5,997,463 A | 12/1999 | Cutrer |
| 6,048,299 A | 4/2000 | Hoffmann |
| 6,066,083 A | 5/2000 | Slater et al. |
| 6,083,148 A | 7/2000 | Williams |
| 6,086,942 A | 7/2000 | Carden, Jr. et al. |
| 6,099,458 A | 8/2000 | Robertson |
| 6,106,517 A | 8/2000 | Zupkas |
| 6,129,670 A | 10/2000 | Burdette et al. |
| 6,132,359 A | 10/2000 | Bolenbaugh |
| 6,159,141 A | 12/2000 | Apple et al. |
| 6,163,947 A | 12/2000 | Coniglione |
| 6,179,768 B1 | 1/2001 | Loffler et al. |
| 6,196,963 B1 | 3/2001 | Williams |
| 6,196,964 B1 | 3/2001 | Loffler et al. |
| 6,210,312 B1 | 4/2001 | Nagy |
| 6,210,315 B1 | 4/2001 | Andrews et al. |
| 6,213,932 B1 | 4/2001 | Schmidt |
| 6,213,976 B1 | 4/2001 | Trerotola |
| 6,221,003 B1 | 4/2001 | Sierocuk et al. |
| 6,224,536 B1 | 5/2001 | Pike |
| 6,248,057 B1 | 6/2001 | Mavity et al. |
| 6,251,059 B1 | 6/2001 | Apple et al. |
| 6,267,718 B1 | 7/2001 | Vitali et al. |
| 6,285,735 B1 | 9/2001 | Sliski et al. |
| 6,287,249 B1 | 9/2001 | Tam et al. |
| 6,299,856 B1 | 10/2001 | DeVore et al. |
| 6,315,979 B1 | 11/2001 | Simon et al. |
| 6,319,188 B1 | 11/2001 | Lovoi |
| 6,320,932 B2 | 11/2001 | Dinsmore |
| 6,320,935 B1 | 11/2001 | Shinar et al. |
| 6,327,490 B1 | 12/2001 | Spetz |
| 6,347,443 B2 | 2/2002 | Coniglione |
| 6,352,500 B1 | 3/2002 | Halpern |
| 6,352,501 B1 | 3/2002 | Urick |
| 6,358,195 B1 | 3/2002 | Green et al. |
| 6,360,116 B1 | 3/2002 | Jackson, Jr. et al. |
| 6,361,487 B1 | 3/2002 | Green et al. |
| 6,366,796 B1 | 4/2002 | Yanof et al. |
| 6,387,034 B1 | 5/2002 | Lee |
| 6,390,967 B1 | 5/2002 | Forman et al. |
| 6,390,968 B1 | 5/2002 | Harmon |
| 6,391,026 B1 | 5/2002 | Hung et al. |
| 6,391,279 B1 | 5/2002 | Singh et al. |
| 6,398,711 B1 | 6/2002 | Green et al. |
| 6,402,677 B1 | 6/2002 | Jacobs |
| 6,413,204 B1 | 7/2002 | Winkler et al. |
| 6,415,921 B2 | 7/2002 | Ye et al. |
| 6,416,531 B2 | 7/2002 | Chen |
| 6,419,621 B1 | 7/2002 | Sioshansi et al. |
| 6,419,866 B1 | 7/2002 | Karl et al. |
| 6,436,026 B1 | 8/2002 | Sioshansi et al. |
| 6,450,937 B1 | 9/2002 | Mercereau et al. |
| 6,450,938 B1 | 9/2002 | Miller |
| 6,471,631 B1 | 10/2002 | Slater et al. |
| 6,477,426 B1 | 11/2002 | Fenn et al. |
| 6,493,419 B1 | 12/2002 | Dinsmore |
| 6,494,835 B1 | 12/2002 | Ciezki et al. |
| 6,500,108 B1 | 12/2002 | Sorensen et al. |
| 6,527,693 B2 | 3/2003 | Munro, III et al. |
| 6,530,873 B1 | 3/2003 | Lee |
| 6,530,875 B1 | 3/2003 | Taylor et al. |
| 6,537,195 B2 | 3/2003 | Forman |
| 6,539,247 B2 | 3/2003 | Spetz |
| 6,551,232 B1 | 4/2003 | Rivard |
| 6,554,756 B1 | 4/2003 | Schaart |
| 6,558,309 B2 | 5/2003 | Hogendijk et al. |
| 6,561,967 B2 | 5/2003 | Schmidt |
| 6,572,526 B1 | 6/2003 | Ford |
| 6,575,888 B2 | 6/2003 | Zamora et al. |
| 6,579,262 B1 | 6/2003 | Mick et al. |
| 6,582,354 B2 | 6/2003 | Ellard |
| 6,582,417 B1 | 6/2003 | Ledesma et al. |
| 6,585,633 B2 | 7/2003 | Vitali et al. |
| 6,589,173 B1 | 7/2003 | Mitragotri |
| 6,589,502 B1 | 7/2003 | Coniglione et al. |
| 6,603,988 B2 | 8/2003 | Dowlatshahi |
| 6,607,476 B1 | 8/2003 | Barnhart |
| 6,607,478 B2 | 8/2003 | Williams |
| 6,608,277 B2 | 8/2003 | Spooner et al. |
| 6,610,013 B1 | 8/2003 | Fenster et al. |
| 6,615,070 B2 | 9/2003 | Lee |
| 6,626,817 B2 | 9/2003 | Luth |
| 6,632,176 B2 | 10/2003 | McIntire et al. |
| 6,638,205 B1 | 10/2003 | Chan et al. |
| 6,638,206 B2 | 10/2003 | Green et al. |
| 6,639,237 B2 | 10/2003 | Pedersen et al. |
| 6,641,518 B2 | 11/2003 | Wolfson et al. |
| 6,648,811 B2 | 11/2003 | Sierocuk et al. |
| 6,652,442 B2 | 11/2003 | Gatto |
| 6,656,107 B1 | 12/2003 | Pedersen et al. |
| 6,659,105 B2 | 12/2003 | Burbank et al. |
| 6,659,933 B2 | 12/2003 | Asano |
| 6,669,621 B2 | 12/2003 | O'Hara et al. |
| 6,673,006 B2 | 1/2004 | Winkler |
| 6,676,590 B1 | 1/2004 | Urick et al. |
| 6,676,595 B1 | 1/2004 | Delfino |
| 6,676,658 B2 | 1/2004 | Burbank et al. |
| 6,679,824 B1 | 1/2004 | Reed et al. |
| 6,682,471 B2 | 1/2004 | Steele, Sr. et al. |
| 6,685,618 B2 | 2/2004 | Tam et al. |
| 6,685,619 B2 | 2/2004 | Halpern et al. |
| 6,689,043 B1 | 2/2004 | McIntire et al. |
| 6,689,811 B2 | 2/2004 | Koumenis et al. |
| 6,692,587 B2 | 2/2004 | Ro et al. |
| 6,695,760 B1 | 2/2004 | Winkler et al. |
| 6,695,787 B2 | 2/2004 | Hogendijk et al. |
| 6,699,171 B2 | 3/2004 | Harmon |
| 6,701,175 B2 | 3/2004 | Dowlatshahi |
| 6,703,375 B2 | 3/2004 | Buchsbaum et al. |
| 6,706,014 B2 | 3/2004 | Banik et al. |
| 6,706,699 B2 | 3/2004 | Wang et al. |
| 6,709,380 B2 | 3/2004 | Green et al. |
| 6,709,381 B2 | 3/2004 | Munro, III |
| 6,712,782 B2 | 3/2004 | Ford |
| 6,712,816 B2 | 3/2004 | Hung et al. |
| 6,713,462 B2 | 3/2004 | Metcalf, III et al. |
| 6,716,156 B2 | 4/2004 | Menuhr et al. |
| 6,727,225 B2 | 4/2004 | Wiley |
| 6,730,013 B1 | 5/2004 | Shank et al. |
| 6,746,392 B2 | 6/2004 | Stiger et al. |
| 6,746,393 B2 | 6/2004 | Mawad |
| 6,746,465 B2 | 6/2004 | Diederich et al. |
| 6,746,661 B2 | 6/2004 | Kaplan |
| 6,749,553 B2 | 6/2004 | Brauckman et al. |
| 6,749,555 B1 | 6/2004 | Winkler et al. |
| 6,752,752 B2 | 6/2004 | Geitz |
| 6,752,753 B1 | 6/2004 | Hoskins et al. |
| 6,755,775 B2 | 6/2004 | Kalas et al. |
| 6,761,679 B2 | 7/2004 | Sajo et al. |
| 6,761,680 B2 | 7/2004 | Terwilliger et al. |
| 6,770,021 B2 | 8/2004 | Halpern |
| 6,773,390 B2 | 8/2004 | McDaniel |
| 6,778,850 B1 | 8/2004 | Adler et al. |
| 6,786,858 B2 | 9/2004 | Terwilliger et al. |
| 6,788,977 B2 | 9/2004 | Fenn et al. |
| 6,790,170 B2 | 9/2004 | Moody et al. |
| 6,792,073 B2 | 9/2004 | Deasy et al. |
| 6,796,936 B2 | 9/2004 | Slater et al. |
| 6,799,075 B2 | 9/2004 | Chornenky et al. |
| 6,800,055 B2 | 10/2004 | Amols et al. |
| 6,809,517 B2 | 10/2004 | McGee et al. |
| 6,811,779 B2 | 11/2004 | Rockwell et al. |
| 6,817,995 B1 | 11/2004 | Halpern |
| 6,820,318 B2 | 11/2004 | Terwilliger et al. |
| 6,824,507 B2 | 11/2004 | Miller |
| 6,824,773 B2 | 11/2004 | Wiley |

(56) References Cited

U.S. PATENT DOCUMENTS

| | | |
|---|---|---|
| 6,837,844 B1 | 1/2005 | Ellard et al. |
| 6,846,282 B1 | 1/2005 | Ford |
| 6,846,283 B2 | 1/2005 | Green et al. |
| 6,847,700 B1 | 1/2005 | Mitra et al. |
| 6,847,838 B1 | 1/2005 | Macey et al. |
| 6,856,668 B1 | 2/2005 | Thomson et al. |
| 6,861,044 B2 | 3/2005 | Simon et al. |
| 6,863,654 B2 | 3/2005 | Zappala et al. |
| 6,865,412 B2 | 3/2005 | Dowlatshahi |
| 6,866,624 B2 | 3/2005 | Chornenky et al. |
| 6,867,305 B2 | 3/2005 | Danishefsky et al. |
| 6,869,390 B2 | 3/2005 | Elliott et al. |
| 6,869,588 B2 | 3/2005 | Weller et al. |
| 6,878,697 B2 | 4/2005 | Metcalf, III et al. |
| 6,890,950 B2 | 5/2005 | Boothman et al. |
| 6,910,999 B2 | 6/2005 | Chin et al. |
| 6,919,067 B2 | 7/2005 | Filler et al. |
| 6,921,769 B2 | 7/2005 | Danishefsky et al. |
| 6,923,754 B2 | 8/2005 | Lubock |
| 6,949,064 B2 | 9/2005 | Lowery et al. |
| 6,953,426 B2 | 10/2005 | Barber et al. |
| 6,955,640 B2 | 10/2005 | Sanders et al. |
| 6,955,641 B2 | 10/2005 | Lubock |
| 6,957,108 B2 | 10/2005 | Turner et al. |
| 6,960,572 B2 | 11/2005 | Shakespeare et al. |
| 6,965,847 B2 | 11/2005 | Wessol et al. |
| 6,967,198 B2 | 11/2005 | Benedict et al. |
| 6,976,949 B2 | 12/2005 | Winkler et al. |
| 6,985,557 B2 | 1/2006 | Jaafar |
| 6,986,880 B2 | 1/2006 | Coniglione et al. |
| 6,987,835 B2 | 1/2006 | Lovoi |
| 6,989,486 B2 | 1/2006 | Lovoi et al. |
| 6,994,688 B2 | 2/2006 | Brauckman et al. |
| 6,997,861 B2 | 2/2006 | Halpern et al. |
| 6,997,862 B2 | 2/2006 | Terwilliger et al. |
| 7,008,368 B2 | 3/2006 | Terwilliger et al. |
| 7,008,633 B2 | 3/2006 | Yang et al. |
| 7,009,054 B2 | 3/2006 | Wang et al. |
| 7,018,371 B2 | 3/2006 | Forman |
| 7,019,139 B2 | 3/2006 | Metcalf, III et al. |
| 7,025,717 B2 | 4/2006 | Tarone et al. |
| 7,031,432 B2 | 4/2006 | Geitz |
| 7,037,252 B2 | 5/2006 | Flanagan et al. |
| 7,041,046 B2 | 5/2006 | Forman |
| 7,041,047 B2 | 5/2006 | Gellman et al. |
| 7,041,048 B2 | 5/2006 | Drobnik et al. |
| 7,041,109 B2 | 5/2006 | Dowlatshahi |
| 7,048,717 B1 | 5/2006 | Frassica |
| 7,060,020 B2 | 6/2006 | Terwilliger et al. |
| 7,064,211 B2 | 6/2006 | Kowalczyk et al. |
| 7,066,872 B2 | 6/2006 | Waksman et al. |
| 7,067,475 B2 | 6/2006 | Cerretti et al. |
| 7,070,554 B2 | 7/2006 | White et al. |
| 7,074,291 B2 | 7/2006 | Terwilliger et al. |
| 7,074,408 B2 | 7/2006 | Fanslow, III et al. |
| 7,077,800 B2 | 7/2006 | Gross et al. |
| 7,083,566 B2 | 8/2006 | Tornes et al. |
| 7,091,343 B2 | 8/2006 | Bebbington et al. |
| 7,094,198 B2 | 8/2006 | Terwilliger et al. |
| 7,107,089 B2 | 9/2006 | Lee |
| 7,109,505 B1 | 9/2006 | Sliski et al. |
| 7,115,589 B2 | 10/2006 | Weigele et al. |
| 7,115,651 B2 | 10/2006 | Danishefsky et al. |
| 7,118,523 B2 | 10/2006 | Loffler et al. |
| 7,118,524 B2 | 10/2006 | Rivard |
| 7,122,552 B2 | 10/2006 | Ledford |
| 7,127,033 B2 | 10/2006 | Lovoi et al. |
| 7,130,380 B2 | 10/2006 | Lovoi et al. |
| 7,131,942 B2 | 11/2006 | Taylor et al. |
| 7,132,427 B2 | 11/2006 | Wang et al. |
| 7,132,533 B2 | 11/2006 | Benedict et al. |
| 7,158,612 B2 | 1/2007 | Rusch et al. |
| 7,171,253 B2 | 1/2007 | Dowlatshahi |
| 7,175,635 B2 | 2/2007 | Loser |
| 7,175,849 B2 | 2/2007 | Baum et al. |
| 7,179,826 B2 | 2/2007 | Bebbington et al. |
| 7,179,912 B2 | 2/2007 | Halbrook et al. |
| 7,182,726 B2 | 2/2007 | Williams et al. |
| 7,187,800 B2 | 3/2007 | Hibbard |
| 7,190,895 B1 | 3/2007 | Groves et al. |
| 7,192,972 B2 | 3/2007 | Kowalczyk et al. |
| 7,196,090 B2 | 3/2007 | Connolly et al. |
| 7,198,783 B2 | 4/2007 | Morris et al. |
| 7,200,203 B2 | 4/2007 | Cocks et al. |
| 7,201,715 B2 | 4/2007 | Burdette et al. |
| 7,201,890 B2 | 4/2007 | Goldenberg |
| 7,201,906 B2 | 4/2007 | Cheung |
| 7,204,986 B2 | 4/2007 | Cheung |
| 7,204,987 B2 | 4/2007 | Cheung |
| 7,204,988 B2 | 4/2007 | Cheung |
| 7,208,158 B2 | 4/2007 | Cheung |
| 7,208,500 B2 | 4/2007 | Lou et al. |
| 7,208,517 B1 | 4/2007 | Winn et al. |
| 7,211,039 B2 | 5/2007 | Lamoureux |
| 7,211,055 B2 | 5/2007 | Diederich et al. |
| 7,214,368 B2 | 5/2007 | Rasmussen et al. |
| 7,214,377 B2 | 5/2007 | Cheung |
| 7,217,242 B2 | 5/2007 | Alam et al. |
| 7,228,579 B2 | 6/2007 | Tidwell |
| 7,252,630 B2 | 8/2007 | Terwilliger et al. |
| 7,267,643 B2 | 9/2007 | Koster et al. |
| 7,313,430 B2 | 12/2007 | Urquhart et al. |
| 7,322,928 B2 | 1/2008 | Reed et al. |
| 7,322,929 B2 | 1/2008 | Lovoi |
| 7,329,242 B2 | 2/2008 | Peery |
| 7,344,490 B2 | 3/2008 | Shaw et al. |
| 7,344,533 B2 | 3/2008 | Pearson et al. |
| 7,351,193 B2 | 4/2008 | Forman et al. |
| 7,354,391 B2 | 4/2008 | Stubbs |
| 7,357,770 B1 | 4/2008 | Cutrer et al. |
| 7,361,134 B2 | 4/2008 | Rozenfeld et al. |
| 7,361,135 B2 | 4/2008 | Drobnik et al. |
| 7,396,354 B2 | 7/2008 | Rychnovsky et al. |
| 7,399,977 B2 | 7/2008 | Rink et al. |
| 7,410,458 B2 | 8/2008 | Bray et al. |
| 7,419,487 B2 | 9/2008 | Johnson et al. |
| 7,422,588 B2 | 9/2008 | Mulier et al. |
| 7,425,194 B2 | 9/2008 | Baltas et al. |
| 7,725,155 B2 | 5/2010 | Dowlatshahi |
| 2001/0055589 A1 | 12/2001 | Smilowitz et al. |
| 2002/0010500 A1 | 1/2002 | Chen |
| 2002/0010502 A1 | 1/2002 | Trachtenberg |
| 2002/0077521 A1 | 6/2002 | Green et al. |
| 2002/0091315 A1 | 7/2002 | Spetz |
| 2002/0151778 A1 | 10/2002 | Dowlatshahi |
| 2002/0169354 A1 | 11/2002 | Munro, III |
| 2002/0169410 A1 | 11/2002 | Ford |
| 2002/0177748 A1 | 11/2002 | Munro, III |
| 2002/0193654 A1 | 12/2002 | Mawad |
| 2003/0018233 A1 | 1/2003 | Miller |
| 2003/0045769 A1 | 3/2003 | Kalas et al. |
| 2003/0083566 A1 | 5/2003 | Dowlatshahi |
| 2003/0092956 A1 | 5/2003 | Williams |
| 2003/0092958 A1 | 5/2003 | Terwilliger et al. |
| 2003/0097035 A1 | 5/2003 | Tucker et al. |
| 2003/0130711 A1 | 7/2003 | Pearson et al. |
| 2003/0153850 A1 | 8/2003 | Davis et al. |
| 2003/0158515 A1 | 8/2003 | Gonzalez et al. |
| 2003/0171637 A1 | 9/2003 | Terwilliger et al. |
| 2003/0171638 A1 | 9/2003 | Schaart |
| 2003/0176759 A1 | 9/2003 | Hogendijk et al. |
| 2003/0212302 A1 | 11/2003 | Rozenfeld et al. |
| 2003/0229282 A1 | 12/2003 | Burdette et al. |
| 2003/0233136 A1 | 12/2003 | Williams et al. |
| 2004/0010290 A1 | 1/2004 | Schroeppel et al. |
| 2004/0068157 A1 | 4/2004 | Gellman et al. |
| 2004/0077919 A1 | 4/2004 | Drobnik et al. |
| 2004/0102671 A1 | 5/2004 | Terwilliger et al. |
| 2004/0106840 A1 | 6/2004 | Kindlein et al. |
| 2004/0109823 A1 | 6/2004 | Kaplan |
| 2004/0111004 A1 | 6/2004 | Loffler et al. |
| 2004/0116767 A1 | 6/2004 | Lebovic et al. |
| 2004/0116914 A1* | 6/2004 | Dowlatshahi .................. 606/10 |
| 2004/0133195 A1 | 7/2004 | Solomon |

(56) References Cited

U.S. PATENT DOCUMENTS

| | | |
|---|---|---|
| 2004/0138515 A1 | 7/2004 | White et al. |
| 2004/0152973 A1 | 8/2004 | Lee |
| 2004/0162458 A1 | 8/2004 | Green et al. |
| 2004/0186340 A1 | 9/2004 | Reed et al. |
| 2004/0192998 A1 | 9/2004 | Brauckman et al. |
| 2004/0210101 A1 | 10/2004 | Winkler |
| 2004/0225176 A1 | 11/2004 | Flanagan et al. |
| 2004/0230087 A1 | 11/2004 | Terwilliger et al. |
| 2004/0243200 A1 | 12/2004 | Turner et al. |
| 2004/0254418 A1 | 12/2004 | Munro et al. |
| 2005/0000525 A1 | 1/2005 | Klimberg et al. |
| 2005/0004507 A1 | 1/2005 | Schroeppel et al. |
| 2005/0011526 A1 | 1/2005 | Forman et al. |
| 2005/0027156 A1 | 2/2005 | Pulido et al. |
| 2005/0027196 A1 | 2/2005 | Fitzgerald |
| 2005/0031648 A1 | 2/2005 | Brin et al. |
| 2005/0049508 A1 | 3/2005 | Forman et al. |
| 2005/0070753 A1 | 3/2005 | Forman et al. |
| 2005/0075529 A1 | 4/2005 | Pedersen et al. |
| 2005/0080313 A1 | 4/2005 | Stewart et al. |
| 2005/0080340 A1 | 4/2005 | Stewart et al. |
| 2005/0085681 A1 | 4/2005 | Stubbs et al. |
| 2005/0096515 A1 | 5/2005 | Geng |
| 2005/0101824 A1 | 5/2005 | Stubbs |
| 2005/0101825 A1 | 5/2005 | Winkler et al. |
| 2005/0101826 A1 | 5/2005 | Bray et al. |
| 2005/0107653 A1 | 5/2005 | Patrick et al. |
| 2005/0119725 A1 | 6/2005 | Wang et al. |
| 2005/0124844 A1 | 6/2005 | Forman |
| 2005/0184424 A1 | 8/2005 | Ferguson |
| 2005/0187422 A1 | 8/2005 | Maschke |
| 2005/0191207 A1 | 9/2005 | Terwilliger et al. |
| 2005/0251235 A1 | 11/2005 | Schlorff et al. |
| 2005/0261541 A1 | 11/2005 | Henderson et al. |
| 2005/0267319 A1 | 12/2005 | White et al. |
| 2005/0277802 A1 | 12/2005 | Larsen et al. |
| 2006/0017009 A1 | 1/2006 | Rink et al. |
| 2006/0023843 A1 | 2/2006 | Kusch |
| 2006/0058568 A1 | 3/2006 | Gross et al. |
| 2006/0063961 A1 | 3/2006 | Drobnik et al. |
| 2006/0063962 A1 | 3/2006 | Drobnik et al. |
| 2006/0067467 A1* | 3/2006 | Chornenky et al. ............. 378/65 |
| 2006/0069298 A1 | 3/2006 | Terwilliger et al. |
| 2006/0074303 A1 | 4/2006 | Chornenky et al. |
| 2006/0089520 A1 | 4/2006 | Terwilliger et al. |
| 2006/0100475 A1 | 5/2006 | White et al. |
| 2006/0100476 A1 | 5/2006 | Biscotti |
| 2006/0111605 A1 | 5/2006 | Larsen et al. |
| 2006/0116546 A1 | 6/2006 | Eng |
| 2006/0122452 A1 | 6/2006 | van't Hooft |
| 2006/0167332 A1 | 7/2006 | Bray |
| 2006/0173232 A1 | 8/2006 | Lovoi et al. |
| 2006/0173233 A1 | 8/2006 | Lovoi |
| 2006/0173235 A1 | 8/2006 | Lim et al. |
| 2006/0173236 A1 | 8/2006 | White et al. |
| 2006/0183959 A1 | 8/2006 | Sioshansi et al. |
| 2006/0183960 A1 | 8/2006 | Sioshansi et al. |
| 2006/0184018 A1 | 8/2006 | Cox et al. |
| 2006/0224035 A1 | 10/2006 | Russell et al. |
| 2006/0235260 A1 | 10/2006 | Mourtada et al. |
| 2006/0235365 A1 | 10/2006 | Terwilliger et al. |
| 2006/0241332 A1 | 10/2006 | Klein et al. |
| 2006/0241727 A1 | 10/2006 | Dowlatshahi |
| 2007/0015837 A1 | 1/2007 | Kun et al. |
| 2007/0016062 A1 | 1/2007 | Park et al. |
| 2007/0021643 A1 | 1/2007 | Lamoureux et al. |
| 2007/0027352 A1 | 2/2007 | Mourtada et al. |
| 2007/0038014 A1 | 2/2007 | Cox et al. |
| 2007/0049786 A1 | 3/2007 | Edmundson |
| 2007/0055090 A1 | 3/2007 | Neustadter et al. |
| 2007/0074347 A1 | 4/2007 | Coppens et al. |
| 2007/0075277 A1 | 4/2007 | Smith et al. |
| 2007/0084474 A1 | 4/2007 | Rivard |
| 2007/0100229 A1 | 5/2007 | Dowlatshahi |
| 2007/0106108 A1 | 5/2007 | Hermann et al. |
| 2007/0123815 A1 | 5/2007 | Mark |
| 2007/0135873 A1 | 6/2007 | Johansson et al. |
| 2007/0140426 A1 | 6/2007 | Axelrod et al. |
| 2007/0142694 A1 | 6/2007 | Cutrer et al. |
| 2007/0142695 A1 | 6/2007 | White et al. |
| 2007/0149571 A1 | 6/2007 | Stein et al. |
| 2007/0167665 A1 | 7/2007 | Hermann et al. |
| 2007/0173680 A1 | 7/2007 | Rioux et al. |
| 2007/0219488 A1 | 9/2007 | Francescatti |
| 2007/0270627 A1 | 11/2007 | Cutrer et al. |
| 2007/0288075 A1 | 12/2007 | Dowlatshahi |
| 2008/0004478 A1 | 1/2008 | Francescatti et al. |
| 2008/0004524 A1 | 1/2008 | Francescatti et al. |
| 2008/0004543 A1 | 1/2008 | Davies |
| 2008/0009658 A1 | 1/2008 | Smith et al. |
| 2008/0009659 A1 | 1/2008 | Smith et al. |
| 2008/0071132 A1 | 3/2008 | Lamoureux et al. |
| 2008/0086026 A1 | 4/2008 | Keppel et al. |
| 2008/0091056 A1 | 4/2008 | Kaplan |
| 2008/0103104 A1 | 5/2008 | Moore et al. |
| 2008/0118518 A1 | 5/2008 | Cirrito et al. |
| 2008/0154085 A1 | 6/2008 | Jervis et al. |
| 2008/0154086 A1 | 6/2008 | Stubbs |
| 2008/0177127 A1 | 7/2008 | Allan et al. |
| 2008/0185314 A1 | 8/2008 | Tomasello et al. |
| 2008/0188841 A1 | 8/2008 | Tomasello et al. |
| 2008/0188842 A1 | 8/2008 | Tomasello et al. |
| 2008/0194985 A1 | 8/2008 | Nicoson et al. |
| 2008/0208052 A1 | 8/2008 | LePivert et al. |
| 2008/0214887 A1 | 9/2008 | Heanue et al. |
| 2008/0221384 A1 | 9/2008 | Chi Sing et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0293994 A1 | 11/2008 | Francescatti et al. |
| 2008/0300443 A1 | 12/2008 | Lovoi |
| 2008/0300445 A1 | 12/2008 | Francescatti et al. |
| 2008/0306322 A1 | 12/2008 | Jervis et al. |
| 2008/0306323 A1 | 12/2008 | Jervis et al. |
| 2009/0030258 A1 | 1/2009 | Axelrod et al. |
| 2010/0222647 A1* | 9/2010 | Hashimshony et al. ...... 600/301 |

OTHER PUBLICATIONS

A Novel real-time dosimetry technique based on radiation-induced surface activation, H. Tomozawa et al., Apr. 27, 2006.

Advanced X-Ray Technology, Inc., website, downloaded from http://www.axt-medical.com/products/softray, Jan. 15, 2008.

Advanced X-Ray Technology Devices—Description, website, http://www.axt-medical.com, downloaded Nov. 29, 2007.

Brachytherapy—definition, RadiologyInfo website, http://www.radiologyinfo/org/en/info.cfm?pg=brachy&bhcp=1, downloaded Nov. 29, 2007.

Brachytherapy—Wikipedia definition, website, http://en.wikipedia.org/wiki/Brachytherapy, downloaded Nov. 29, 2007.

Breast Cancer—defintion, RadiologyInfo website, http://www.radiologyinfo/org/en/info.cfm?pg=breastcancer , downloaded Nov. 29, 2007.

Critical Technology for In-Space Application of Nuclear Thermal Propulsion—Real-Time Micro-Miniature Dosimeter, NASA SBIR 2005 Solicitation, website, http://sbir.gsfc.nasa.gov/SBIR/abstracts/05/sbir/phase1/sbir-05-1-X10.03-8601.html, downloaded Nov. 29, 2007.

Dosimeter—Wikipedia definition, website, http://en.wikipedia.org/wiki/Dosimeter, downloaded Nov. 29, 2007.

Dosimetrists—definition, RadiologyInfo website, http://www.radiologyinfo.org/en/glossary/glossary1.cfm?Term=dosimetrist&bhcp=1, downloaded Nov. 29, 2007.

HDR Brachytherapy Article, website, http://www.cancercenter.com/conventional-cancer-treatment/hdr-brachytherapy.cfm, website, downloaded Nov. 29, 2007.

MammoSite 5-Day Target Radiation Therapy: How It Works, website, http://www.mammosite.com/breast-lumpectomy/ow-it-works.cfm, downloaded Nov. 29, 2007.

(56) References Cited

OTHER PUBLICATIONS

Neutron Spectrometer, Real-Time Dosimeter and Methodology Using Three-Dimensional Optical Memory, website, http://otl.georgetown.edu/industry/inventions/moma430503.html, downloaded Nov. 29, 2007.

Portable Waterphantom Scanning System, website, downloaded from http://www.multidata-systems.com/rtdwph.asp?wph=port, downloaded Nov. 29, 2007.

RTD (Realtime Dosimetry System), website, downloaded from http://www.multidata-systems.com/rtd_prodpg.asp, downloaded Nov. 29, 2007.

Source 1 X-Ray, website, downloaded from http://www.source1xray.com/glenbrook_detail.html, Jan. 15, 2008.

Stereotactic-guided laser-induced interstitial thermotherapy (SLITT) in gliomas with interoperative morphologic monitoring in open MRI—Abstract, Lumenta, Christiano et al. (Proc. SPIE vol. 4156, Jan. 2001.

Wallet Card Dosimeters, website, downloaded from http://www.stanforddosimetery.com/SIRAD/walletdosimeter.html, Nov. 29, 2007.

X-ray scalpel—new device for target x-ray brachytherapy and stereotactic radiosurgery—Abstract, Gutman, George et al., Mar. 2007.

* cited by examiner

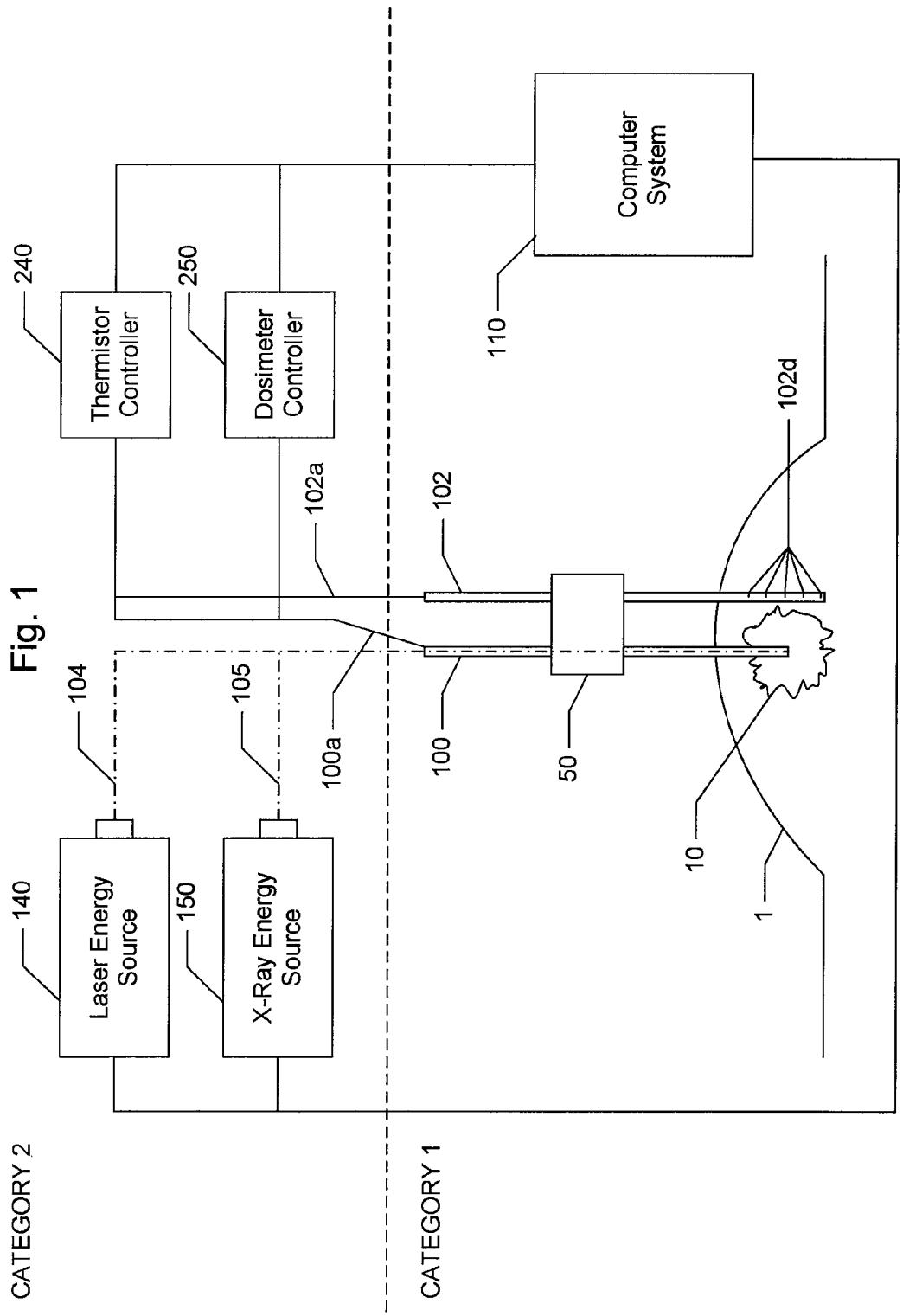

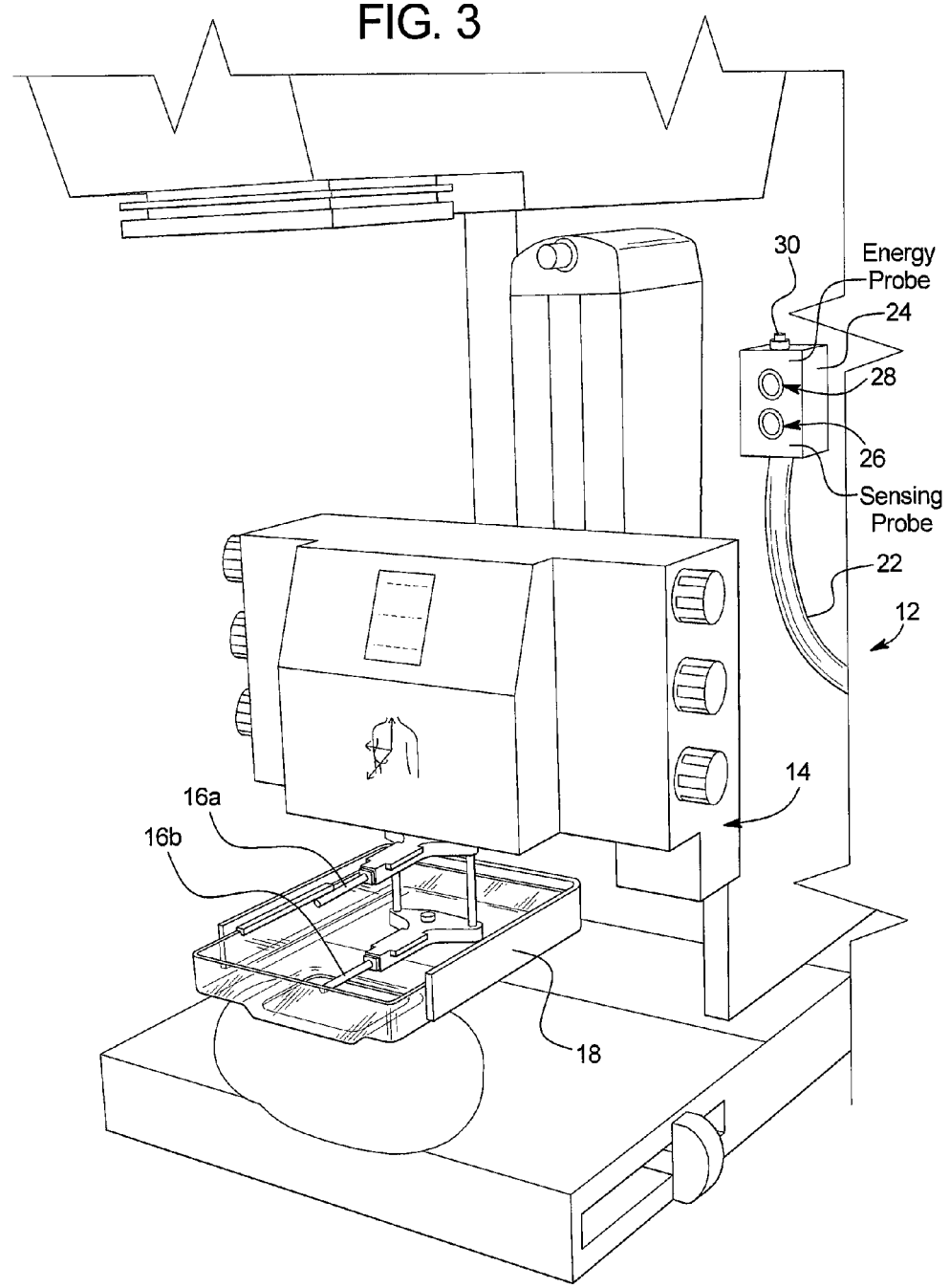

METHODS AND APPARATUS FOR PERFORMING INTERSTITIAL LASER THERAPY AND INTERSTITIAL BRACHYTHERAPY

PRIORITY CLAIM

This application is a non-provisional application of, claims priority to, and the benefit of U.S. Provisional Patent Application No. 61/177,861, filed May 13, 2009, the entire contents of which are incorporated herein by reference.

COPYRIGHT NOTICE

A portion of the disclosure of this patent document contains or may contain material which is subject to copyright protection. The copyright owner has no objection to the photocopy reproduction by anyone of the patent document or the patent disclosure in exactly the form it appears in the Patent and Trademark Office patent file or records, but otherwise reserves all copyright rights whatsoever.

DESCRIPTION

The present disclosure relates in general to a system and methods for applying therapeutic energy to a tissue mass, and in particular to an apparatus for applying x-ray energy and laser energy to a tumor mass and monitoring the dose of x-ray energy and temperature of the tissue adjacent to the tumor mass.

BACKGROUND

Percutaneous in situ or on-site laser therapy treatment of tissue such as tumors and in particular malignant breast tumors can be more readily performed today because tissue abnormalities such as tumors are being detected at earlier stages. Moreover, other treatment techniques can be performed in similarly early stages of the development of tissue abnormalities, such as the application of x-ray energy to a tissue abnormality. Tissue abnormalities such as breast cancer and other cancers or tumors detected early in development can be effectively treated or destroyed using an ablative agent such as laser energy without conventional surgery.

Interstitial laser treatments of tissue (such as tumors) including malignant tumors (such as breast, liver, brain, and neck tumors), have been in development for more than a decade. For example, U.S. Pat. No. 5,169,396, U.S. Pat. No. 5,222,953, U.S. Pat. No. 5,569,240, U.S. Pat. No. 5,853,366, U.S. Pat. No. 6,603,988, U.S. Pat. No. 6,701,175, U.S. Pat. No. 6,865,412, U.S. Pat. No. 7,041,109, and U.S. Pat. No. 7,171,253 disclose various apparatus and methods for applying laser energy directly to a tissue abnormality. Certain of these patents disclose a laser source for generating ablative laser energy to be applied to the tissue abnormality. Certain of these patents also disclose thermal probes including thermistors for detecting the temperature of tissue adjacent to tissue abnormalities.

In certain known treatment regimens, interstitial laser therapy is followed or preceded by chemotherapy, radiation therapy, or both. Currently available radiation therapy techniques require invasive steps beyond the minimally invasive techniques for performing interstitial laser therapy. For example, one radiation therapy technique includes creating an incision to enable radioactive seeds to be deposited at or near the tissue abnormality to be treated.

Furthermore, in certain other known treatment regimes, an apparatus for delivering energy to a tissue mass to be treated (such as a tumor mass) includes a catheter inserted in the vicinity of the tissue mass. In certain of such treatment regimes, the catheter is configured to maintain a cavity created as the tissue mass to be treated is destroyed (i.e., as the tissue mass is ablated). For example, in certain treatment regimes, the catheter includes a balloon which is inflated during treatment to maintain the cavity created by ablation of the tissue mass.

There is a need for a system to enable an integrated delivery modality that can deliver radiation to a treatment site in a controlled, minimally invasive way. There is a further need for devices for facilitating interstitial brachytherapy in a minimally invasive way. There is a further need for a therapeutic system including a plurality of components for applying therapeutic laser energy and therapeutic x-ray energy without removing or inserting one or more additional percutaneous components. There is a further need for a therapeutic system which enables delivery of radiation to a treatment site without the use of a catheter or balloon to maintain a cavity formed during treatment.

SUMMARY

Various embodiments of the therapeutic system disclosed herein enable an operator to conduct either interstitial laser therapy, brachytherapy, or both interstitial laser therapy and brachytherapy on the same tissue of interest. The disclosed system includes two general categories of components. The first category includes components usable to perform both interstitial laser therapy and brachytherapy. The second category includes components usable to perform either interstitial laser therapy or brachytherapy, but not both. For purposes of brevity of this application, the tissue of interest will sometimes be referred to as the "treated tissue" and will sometimes be referred to as the "tumor." It should be appreciated that in different embodiments, the therapeutic energy system disclosed enables therapeutic energy to be applied to tissue other than tumors, or to tumors in locations of the body other than the breasts.

In one embodiment, the first category of components of the therapeutic system disclosed herein (i.e., the components usable to perform both interstitial laser therapy and brachytherapy) includes an energy probe configured to be positioned in the tumor, a sensing probe configured to detect a plurality of temperatures and a plurality of dosage amounts, at least one probe holder configured to position the energy probe and the sensing probe with respect to a stereotactic imaging device, and a computer configured to (a) control the amount of laser energy applied to the tumor; (b) control the amount of x-ray energy applied to the tumor; (c) monitor the temperature of the tissue adjacent to the tumor based on a plurality of received signals indicating a plurality of detected temperatures; and (d) monitor the dosage applied to the tumor mass based on a plurality of received signals indicating a plurality of detected dosage amounts. In this embodiment, the second category of components (i.e., the components usable to perform either interstitial laser therapy or brachytherapy but not both) includes a laser energy source, an x-ray energy source, an optical fiber configured to be connected to the laser energy source and to be removably inserted in the energy probe, an optical fiber configured to be connected to the x-ray energy source and to be removably inserted in the energy probe, and at least one controller configured to (a) receive a plurality of electrical signals from a plurality of sensors; (b) convert the received electric signals into a plurality of temperatures and a plurality of dosage amounts; and (c) send a plurality of signals indicating the converted temperatures and dosage amounts to the computer of the first category of components.

In one embodiment, the first category of components and the second category of components of the therapeutic system disclosed herein enable an operator to perform interstitial laser therapy before performing brachytherapy. Specifically, the therapeutic system disclosed enables an operator to configure the components of the first category of components with the interstitial laser therapy-specific components of the second category of components to apply controlled amounts therapeutic laser energy directly to a tumor and to monitor the temperature of the tissue adjacent to the tumor. In this embodiment, the therapeutic system then enables the operator to replace the interstitial laser therapy-specific components of the second category of components with the brachytherapy-specific components and to apply controlled amounts of therapeutic x-ray energy and monitor the dose(s) applied to the tumor.

In an alternative embodiment, the therapeutic system disclosed herein enables an operator to perform brachytherapy prior to performing interstitial laser therapy by utilizing the components of the first category of components with the brachytherapy-specific components of the second category of components to apply x-ray energy until a specific dosage is achieved. In this embodiment, the disclosed system enables the operator to remove the brachytherapy-specific components and utilize the interstitial laser therapy-specific components to apply laser energy until a specified tissue temperature is achieved for tissue adjacent to the tumor mass.

In one embodiment, the components of the system disclosed herein do not include any device or mechanism for maintaining a cavity formed during application of energy to treated tissue. In one such embodiment, the energy probe is configured such that the diameter of the energy probe is substantially constant throughout the length of the energy probe. In one embodiment, the diameter of the probe is relatively small compared to the diameter of the treated tissue. In this embodiment, the structure of the probe itself does not provide an artificial boundary to a cavity formed around the treated tissue. Thus, it should be appreciated that the energy probe in one embodiment is configured not to maintain a cavity formed during application of therapeutic energy—that is, the energy probe does not include a device, such as an inflatable balloon, for maintaining a cavity during treatment.

In one embodiment, the system disclosed herein enables a surgical excision of tissue, such as a lumpectomy, to be performed coincident to application of therapeutic energy to the tissue. In this embodiment, the disclosed system enables an operator to enhance or improve upon results obtainable using such known surgical excision techniques, increasing an overall effectiveness of the treatment of the tissue.

It should be appreciated that combining the components of the first category of components with the brachytherapy-specific components of the second category of components enables the operator to accurately deliver x-ray energy to a tumor. It should be further appreciated that combining the components of the first category of components with the interstitial laser therapy-specific components of the second category of components enables the operator to accurately deliver laser energy to the tumor.

It is therefore an advantage of the present disclosure to provide a therapeutic system for performing interstitial laser therapy and also for performing interstitial brachytherapy wherein the temperature of the tissue adjacent to the tumor mass and the dosage applied to the tumor are respectively monitored.

It is a further advantage of the present disclosure to provide a system for performing interstitial laser therapy and brachytherapy wherein the system includes a plurality of components which are usable to perform both interstitial laser therapy and brachytherapy.

It is a further advantage of the present disclosure to provide a system for performing interstitial laser therapy and brachytherapy which does not require an additional structure, such as a balloon, for maintaining a cavity during treatment.

It is a further advantage of the present disclosure to provide a system for performing interstitial laser therapy and brachytherapy which is usable coincident to known techniques for surgical excision of tissue to enhance the results of a treatment.

It is a further advantage of the present disclosure to provide a therapeutic energy system to enable an operator to apply laser energy and x-ray energy to tissue of interest which saves operator time, saves money on the cost of the components of the disclosed system, decreases patient discomfort, decreases the number of components to be sterilized, increases the accuracy of the point where therapeutic energy is delivered, reduces the number of needle sticks, increases the precision with which amounts of therapeutic energy are applied to tissue of interest such as a tumor mass, and increases the options available to treat tissue of interest such as a tumor mass.

Additional features and advantages of the present invention are described in, and will be apparent from, the following Detailed Description of Exemplary Embodiments and the figures.

DESCRIPTION OF THE DRAWINGS

FIG. 1 is a schematic diagram of the components in two categories of components required to perform both interstitial laser therapy and brachytherapy.

FIG. 3 is a fragmentary perspective view of an imaging unit, a stereotactic device, and an umbilical assembly of an apparatus for performing interstitial laser therapy and brachytherapy.

DETAILED DESCRIPTION OF EXEMPLARY EMBODIMENTS

Figure 2A:
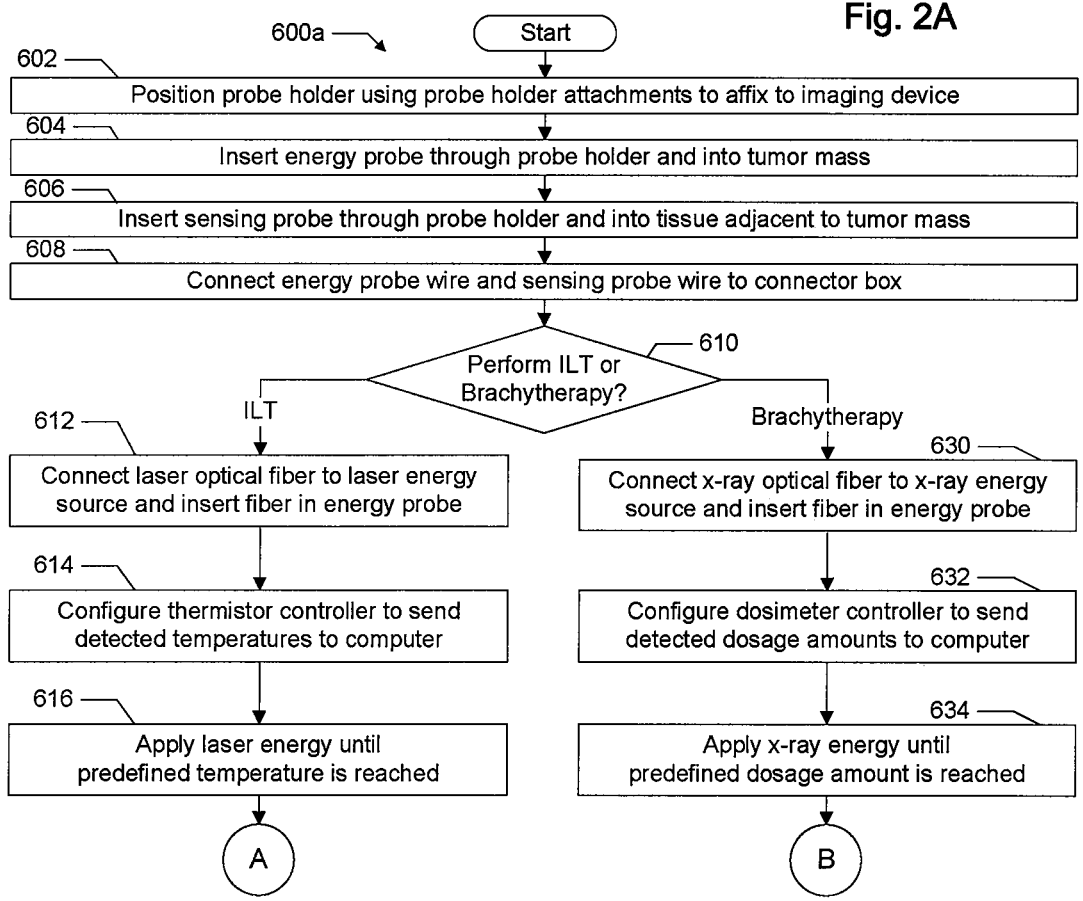
FIGS. 2A and 2B are portions of a flow chart illustrating an example process for performing interstitial laser therapy and brachytherapy using the components of the two disclosed categories.

Referring now to FIG. 1, a schematic diagram of the components of each category of the disclosed system is illustrated. It should be appreciated that the schematic diagram of FIG. 1 is not drawn to scale, nor are the components drawn to accurately represent the shape or size of the component. For example, it should be appreciated that the sensing probe 102 in a preferred embodiment includes a trocar on the percutaneously inserted end, though as illustrated in FIG. 1 the sensing probe does not include such a tip. Moreover, it should be appreciated that solid lines connecting components of the disclosed system indicate an electrical connection. Dashed lines, on the other hand, represent an optical path configured to enable optical energy to be transmitted.

FIG. 1 indicates that the disclosed therapeutic system includes two categories of components, referred to as category one and category two. It should be appreciated that in various embodiments of the therapeutic system disclosed herein, the components of the first category (i.e., components usable to perform both interstitial laser therapy and brachytherapy) include each of the components inserted percutaneously and each of the components used to position the percutaneously positioned components. These embodiments enable an operator to switch between performing interstitial laser therapy and performing brachytherapy without removing or re-inserting any percutaneously positioned components, thus reducing patient discomfort and maintaining repeatable, accurate probe positioning.

Referring first to items of category one, the disclosed system includes a plurality of components usable to perform both interstitial laser therapy and brachytherapy. As illustrated, the components of category one includes an energy probe 100, a sensing probe 102, and at least one probe holder 50. Category one system also includes a computer system 110 configured to receive a plurality of signals indicating quantities of applied energy, and configured to send a plurality of signals indicating changes in the amount of energy applied based on the received signals indicating quantities of applied energy. In the illustrated embodiment, the probe holder 50 is configured to position the energy probe 100 and the sensing probe 102 with respect to a tumor mass 10 of a body part 1 such as a breast. As illustrated, the probe holder 50 is configured to position the energy probe 100 such that the tip of the energy probe 100 is in the center of the tumor mass 10. The probe holder 50 is configured to position the sensing probe 102 such that the plurality of sensors 102d of the sensing probe are adjacent to the tumor mass 10 to sense indicators of applied therapeutic energy of tissue adjacent to the tumor mass 10.

The components included in category two of the disclosed therapeutic system include components usable to perform either interstitial laser therapy or brachytherapy, but not both. In the illustrated embodiment, category two includes a plurality of energy sources such as a laser energy source 140 and an x-ray energy source 150. It should be appreciated that the laser energy source 140 is configured to emit laser energy into an appropriate optical fiber configured to deliver laser energy. It should be further appreciated that the x-ray energy source 150 is configured to emit x-ray energy into an appropriate optical fiber configured to deliver x-ray energy.

Category two also includes a plurality of optical fibers such as a laser optical fiber 104 and an x-ray optical fiber 105. In the illustrated embodiment, the laser optical fiber 104 is configured to be removably attachable to the laser energy source 140. The laser optical fiber 104 is further configured to transmit laser energy along the length of the laser optical fiber and to deliver the energy as light energy at the tip of the laser optical fiber. Similarly, the x-ray optical fiber 105 is configured to be removably attachable to the x-ray energy source 150. The x-ray optical fiber 105 is configured to transmit any x-ray energy emitted by the x-ray energy source 150 along the length of the fiber and to emit the energy as x-ray energy at the tip of the x-ray optical fiber 105.

The components of category two further include a plurality of controllers configured to convert electrical signals to values indicating an amount of energy applied to the tumor mass 10. In the illustrated embodiment, the therapeutic system includes two controllers including a thermistor controller 240 and a dosimeter controller 250. In this embodiment, the thermistor controller 240 is configured to convert a plurality of electrical signals indicating a plurality of detected resistances into a plurality of temperatures. The dosimeter controller 250 is similarly configured to convert a plurality of electrical signals indicating a plurality of changes in charge difference between a plurality of pairs of electrodes of a plurality of dosimeters into a plurality of dosage amounts.

Referring still to FIG. 1, the components of category one are configured to be combined with the components of category two to enable an operator to perform both interstitial laser therapy and brachytherapy. It should be appreciated that the embodiment of the disclosed therapeutic system illustrated in FIG. 1 does not distinguish between whether the therapeutic system is configured to perform interstitial laser therapy or brachytherapy—rather, the illustrated embodiment indicates the interactions between the various components of both categories to perform either interstitial laser therapy or brachytherapy.

In the illustrated embodiment, the energy probe 100 is configured to be positioned in the tumor mass 10 of the body part to be treated 1 using the at least one probe holder 50. The sensing probe 102 is configured to be positioned relative to the energy probe 100 using the at least one probe holder 50.

The energy probe 100 is configured to be connected to the thermistor controller 240 and the dosimeter controller 250 using the energy probe wire 100c. In this embodiment, the energy probe 100 includes at least one thermistor 100e and at least one dosimeter 100e positioned on the tip of the probe 100 and configured to detect a tissue temperature or a dosage amount of the tumor mass 10. It should be appreciated that in various embodiments, the energy probe 100 does not include any sensor 100e such as a thermistor or a dosimeter. In these embodiments, the energy probe does not include an energy probe wire 100c and is not configured to be connected to the thermistor controller or the dosimeter controller.

In the illustrated embodiment, the energy probe 100 is configured to have a substantially constant diameter throughout the length of the probe 100. In the illustrated embodiment, the diameter of the energy probe 100 is relatively small compared to a diameter of the tumor mass 10. Thus, it should be appreciated that in the illustrated embodiment, the energy probe 100 is not configured to maintain a cavity approximating the shape and size of the tumor mass 10 during application of therapeutic energy to the tumor mass 10. That is, the energy probe 100 is not dimensioned (and does not include an additional structure, such as a balloon) to maintain a cavity within the body part 1 approximating the dimensions of the tumor mass 10 to which therapeutic energy is applied.

In one embodiment, a stylet 100b (not shown) is configured to be removable from the cannula 100a after the stylet has been inserted in the tumor mass 10. In this embodiment, removing the stylet 100b enables an optical fiber to be inserted in the energy probe 100. In one embodiment, the laser optical fiber 104 is configured to be inserted in the energy probe 100 after having been attached to the laser energy source 140. In this embodiment, the laser energy probe is configured to deliver laser energy emitted by the laser energy source 140 to the tumor mass 10 in which the energy probe 100 is positioned. In another embodiment, the x-ray optical fiber 105 is configured to be inserted in the energy probe 100 after having been attached to the x-ray energy source 150. In this embodiment, the x-ray optical fiber 105, already connected to the laser energy source, is configured to deliver x-ray energy emitted by the x-ray energy source 150 to the tumor mass 10 in which the energy probe is positioned. It should be appreciated that in one embodiment, the energy probe 100 is configured such that only one of the laser optical fiber 104 and the x-ray optical fiber 105 is insertable in the energy probe 100 at once.

The sensing probe 102 is configured to be connected to the plurality of controllers such as the thermistor controller 240 and the dosimeter controller 250. In the illustrated embodiment, the sensing probe 102 is configured to so connect to the plurality of controllers using the sensing probe wire 102a. As discussed above, the sensing probe wire 102a is configured to carry electrical signals from the plurality of sensors 102d of the sensing probe to the controllers 240 or 250. In one embodiment, the sensing probe wire 102a is also configured to carry a plurality of signals from the dosimeter controller 250 to the dosimeters 102d including energy to maintain charge differences between a plurality of pairs of electrodes the dosimeters.

The computer system 110 is a component of category one, meaning that it is configured to be usable to perform both interstitial laser therapy and brachytherapy. In one embodiment, the computer system 110 includes at least one microprocessor, at least one memory device, at least one display device, at least one input device, at least one interface device for receiving a plurality of signals from a plurality of sensing controllers, and at least one interface device for sending a plurality of signals to a plurality of energy sources. In the illustrated embodiment, the computer system 110 is connected to the thermistor controller 240 and the dosimeter controller 250, and is further connected to the laser energy source 140 and the x-ray energy source 150. In this embodiment, the computer is configured to receive a plurality of signals from the thermistor controller 240 indicating temperatures sensed by the plurality of thermistors of the sensing probe 102. The computer 110 is also configured to receive a plurality of signals from the dosimeter controller 250 indicating dosages detected by the plurality of dosimeters of the sensing probe.

The computer 110 is further configured in one embodiment to store data indicative of the received signals to track the progress of interstitial laser therapy and brachytherapy performed with the disclosed therapeutic system. In one embodiment, the computer system 110 is configured to store each received temperature in a database associated with a patient having the body part 1, and is further configured to store each received dosage amount in the same database. In a further embodiment, the computer 110 is configured to display on the at least one display device a graphical representation of the received signals indicating a plurality of temperatures and a plurality of dosage amounts. In various embodiments, the computer is configured to display a bar graph wherein each bar indicates a temperature of a single thermistor or a dosage of a single dosimeter.

In one embodiment, the computer 110 is further configured to send a plurality of signals to the plurality of energy sources including the laser energy source 140 and the x-ray energy source 150 to change the amount of energy emitted. In one embodiment, if the temperature detected by one or more of the plurality of thermistors of the sensing probe 102 exceeds a predetermined maximum temperature, the computer 110 is configured to send a signal to the laser energy source 140 to cause the laser energy source to stop emitting laser energy. In another embodiment, if a dosage amount detected by one of the dosimeters of the sensing probe 102 exceeds a predetermined maximum dosage amount, the computer 110 is configured to send a signal to the x-ray energy source 150 to cause the x-ray energy source to stop emitting x-ray energy. In various embodiments, once the predetermined maximum temperature or the predetermined maximum dosage amount has been detected, the computer is configured to continue receiving signals indicating temperatures or dosages. In one embodiment, the computer is configured to send a signal to cause the laser energy source 140 to resume generating laser energy when at least one of the thermistors of the sensing probe 102 indicates a temperature below a predefined resume treatment temperature.

It should be appreciated that in various embodiments, one or more components illustrated as belonging to category one in FIG. 1 are configured to be usable to perform interstitial laser therapy or brachytherapy, but not both. For example, in one embodiment, the therapeutic system disclosed herein includes at least two sensing probes. In this embodiment, one of the sensing probes includes a plurality of thermistors for measuring a plurality of temperatures during interstitial laser therapy, and one of the sensing probes includes a plurality of dosimeters for measuring a plurality of dosage amounts during brachytherapy. In this embodiment, between performing interstitial laser therapy and brachytherapy, an operator removes one of the plurality of sensing probes from the at least one probe holder 50 and inserts the other sensing probe in the at least one probe holder 50. It should be appreciated that removing and replacing the sensing probes enables an operator to position the sensing probes at different distances from the energy probe.

In various embodiments, one or more components of category two are configured to be usable to perform both interstitial laser therapy and brachytherapy. For example, in one embodiment the laser optical fiber 104 and the x-ray optical fiber 105 are a single energy optical fiber. In this embodiment, the energy optical fiber and is configured to transmit laser energy and x-ray energy to the tumor mass 10. It should be appreciated that with a single energy optical fiber, an operator in one embodiment removes the energy optical fiber form the laser energy source and connects it to the x-ray energy source, or vice versa, to switch from between performing interstitial laser therapy and brachytherapy.

In various embodiments, the laser energy source 140 and the x-ray energy source 150 are enclosed in a single energy source enclosure. In this embodiment, the laser optical fiber 104 and the x-ray optical fiber 105 are configured to be attachable to different connectors on the same energy source enclosure. In a further embodiment, the combined energy source enclosure includes a single energy connector for connecting the x-ray optical fiber and the laser optical fiber. In this embodiment, an electro-mechanical mechanism within the combined energy source enclosure is configured to switch from emitting laser energy to x-ray energy. In one embodiment, this switch is actuated by a signal sent from the computer 110.

Figure 2B:
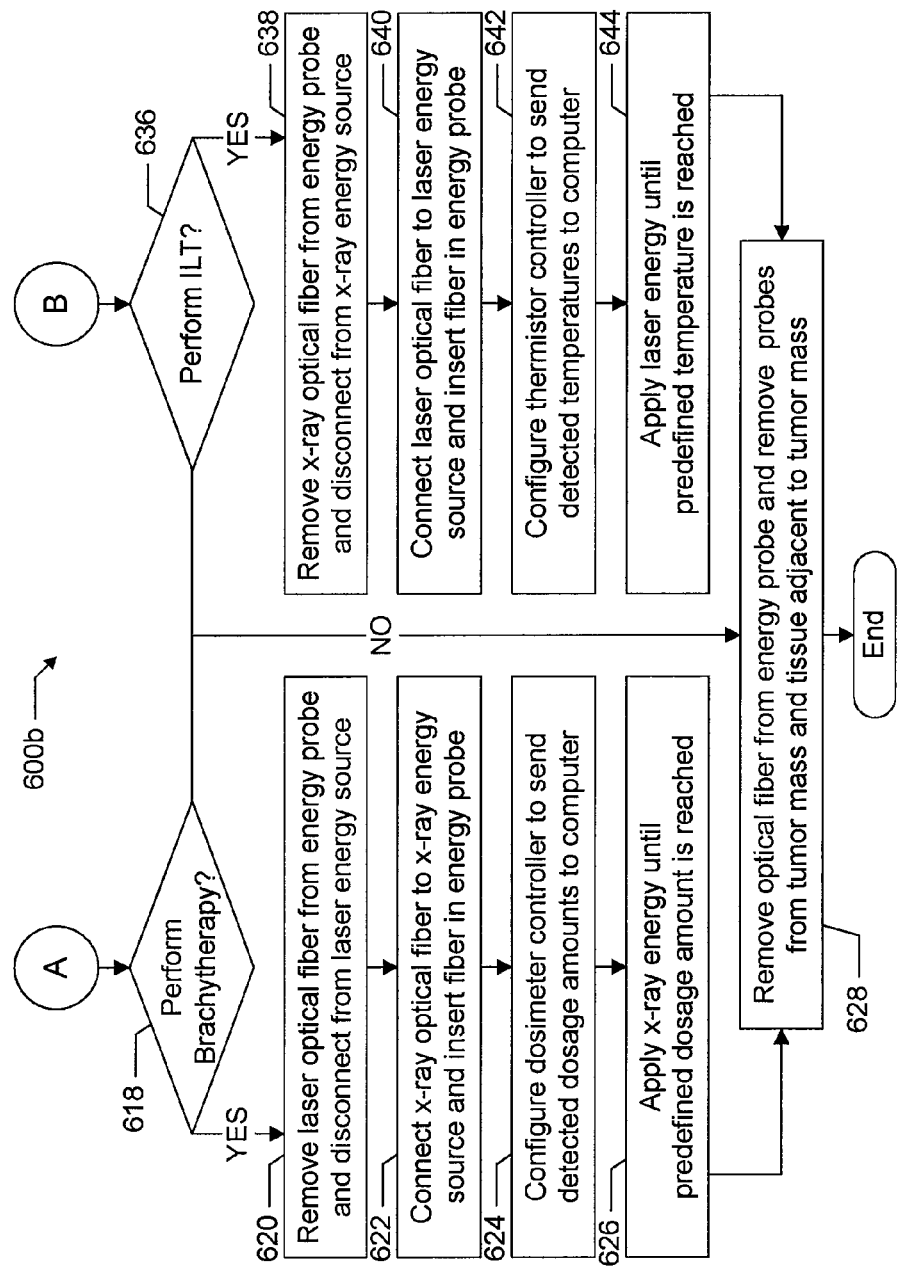

FIGS. 2A and 2B illustrate different components 600a and 600b of a flow chart of an example process for using the therapeutic system disclosed herein to perform both interstitial laser therapy and brachytherapy. Although the example process 600a and 600b for performing interstitial laser therapy and brachytherapy is described with reference to the flow chart illustrated in FIGS. 2A and 2B, it should be appreciated that the system disclosed herein discloses other processes for performing interstitial laser therapy and brachytherapy using the therapeutic system disclosed herein. For example, the order of many of the blocks may be changed, and many of the blocks described are optional.

To begin performing either interstitial laser therapy or brachytherapy using the disclosed therapeutic system, an operator positions the components of category one. Referring to process 600a of FIG. 2A, to do this, the operator positions at least one probe holder using the probe holder attachments of the stereotactic imaging device, as indicated by block 602. Next, the operator positions the energy probe in the probe holders and into the tumor mass, as indicated by block 604. After determining the appropriate position of the sensing probe with respect to the energy probe, the operator inserts the sensing probe through the probe holder and into the tissue adjacent to the tumor mass, as indicated by block 606. The operator in one embodiment completes the set-up of the components of category one by connecting the energy probe wire and the sensing probe wire to the connector box, as indicated by block 608. It should be appreciated that by so configuring the components of the disclosed therapeutic system, the computer is configured to receive the appropriate signals indicating a plurality of dosages and a plurality of temperatures such that an appropriate display can be generated and such that the amount of therapeutic energy applied can be modified accordingly.

As discussed above, the therapeutic system disclosed herein enables an operator to perform both interstitial laser therapy and brachytherapy. Therefore, after the components of category one are configured as discussed with respect to blocks 602, 604, 606, and 608, the operator must determine whether to perform interstitial laser therapy or brachytherapy, as indicated by block 610. It should be appreciated that this determination dictates which of the components of category two are used first. If the operator wishes to perform interstitial laser therapy, the operator connects the laser optical fiber of category two to the laser energy source of category two and inserts the fiber in the energy probe, as indicated by block 612. The operator additionally configures the thermistor controller to send a plurality of signals indicating a plurality of detected temperatures to the computer, as indicated by block 614. Finally, the operator activates the laser energy source, which emits laser energy that is transmitted through the laser optical fiber and applied to the tumor mass, until a predefined temperature or set of temperatures is reached in the tissue adjacent to the tumor mass, as indicated by block 616. In an alternative embodiment, the laser energy source is configured to emit laser energy until a predefined amount of energy has been applied to the tumor mass.

Referring now to FIG. 2B, upon completion of interstitial laser therapy, the operator determines whether to perform brachytherapy, as indicated by block 618. If the operator decides not to perform brachytherapy, the operator removes the optical fiber from the energy probe and removes the energy probe and the sensing probe from the tumor and the tissue adjacent to the tumor, thus finishing therapeutic treatment, as indicated by block 628. If the operator determines that the therapeutic system disclosed should be used to perform brachytherapy, the operator removes the laser optical fiber from the energy probe and disconnects the fiber from the laser energy source, as indicated by block 620. The operator then connects the x-ray optical fiber to the x-ray energy source and inserts the fiber in the energy probe, such that the tip of the optical fiber is even with the tip of the energy probe, as indicated by block 622. The operator configures the dosimeter controller to send a plurality of detected dosage amounts detected by the plurality of dosimeters of the sensing probe to the computer, as indicated by block 624. Finally, the operator applies x-ray energy until a predefined dosage amount is detected by the dosimeters of the sensing probe, as indicated by block 626. Once the predefined dosage amounts have been detected and the x-ray energy source has stopped emitting x-ray energy through the x-ray optical fiber, the operator removes the optical fiber from the energy probe, removes the probes from the tumor mass and the tissue adjacent to the tumor mass, and finishes therapeutic treatment, as indicated by block 628.

Referring again to FIG. 2A, if, after initially configuring the components of category one, the operator determines that brachytherapy should be performed first, as indicated by block 610, the operator connects the x-ray optical fiber to the x-ray energy source and inserts the fiber in the energy probe, as indicated by block 630. The operator configures the dosimeter controller to send a plurality of signals indicating a plurality of detected dosage amounts to the computer for monitoring the progress of the brachytherapy treatment, as indicated by block 632. The operator then performs brachytherapy by activating the x-ray energy source to apply x-ray energy until a predefined dosage amount is detected in the tissue adjacent to the tumor mass, as indicated by block 634.

Referring again to FIG. 2B, upon completion of the brachytherapy treatment described, the operator determines whether to perform interstitial laser therapy, as indicated by block 636. If the operator determines that such interstitial laser therapy is not necessary, the operator removes the optical fiber from the energy probe and removes the energy probe and the sensing probe from the tumor mass and from the tissue adjacent to the tumor mass, as indicated by block 628. If, however, the operator determines that interstitial laser therapy following brachytherapy is appropriate, the operator removes the x-ray optical fiber from the energy probe and disconnects the x-ray optical fiber from the x-ray energy source, as indicated by block 638. The operator then connects the laser optical fiber to the laser energy source and inserts the laser optical fiber in the energy probe, indicated by block 640. The operator configures the thermistor controller to send a plurality of signals indicating a plurality of detected temperatures to the computer to enable the operator to monitor the progress of the interstitial laser therapy, as indicated by block 642. Finally, the operator causes the laser energy source to emit laser energy, such that laser energy is applied to the tumor mass until a predefined temperature is detected by the thermistors in the tissue adjacent to the tumor mass, as indicated by block 644. When the determined temperatures have been reached, the operator removes the optical fiber from the energy probe and removes the probes from the tumor mass and from the tissue adjacent to the tumor mass, as indicated by block 628.

It should be appreciated that in various embodiments, the process illustrated by portions 600a and 600b includes performing each of interstitial laser therapy and brachytherapy more than once, until the operator determines that the appropriate amount and type of therapeutic energy has been applied to the tumor mass.

FIG. 3 illustrates an embodiment of an imaging unit usable with a stereotactic device and further usable with the components disclosed herein to perform both interstitial laser therapy and brachytherapy. Specifically, FIG. 3 illustrates an imaging device or unit such as a conventional rotatable or positionable digital mammography device or unit 12. The mammography unit 12 includes a suitable stereotactic device or unit 14. It should be appreciated that the imaging device or unit may be any suitable unit or device including but not limited to x-ray, ultrasound, or magnetic resource imaging devices. It should also be appreciated that the stereotactic device or unit may be any suitable device or unit. The illustrated stereotactic device 14 includes aligned extendable upper (or first) and lower (or second) probe holder attachments 16a and 16b, respectively, suitably attached at the bottom of the stereotactic device 14. The illustrated stereotactic device 14 includes a compression plate 18 suitably attached at the bottom of the stereotactic device 14 below the upper and lower biopsy needle holders 16a and 16b. For ease of illustration, FIG. 3 shows a saline bag instead of a body part (such as a breast) containing the tissue which would be treated using the interstitial laser energy treatment apparatus.

FIG. 3 further illustrates an umbilical assembly including an umbilical cable 22 and a connector box 24. In the illustrated embodiment, the umbilical assembly includes a plurality of conductors to connect various ones of the components disclosed herein to a plurality of the disclosed components located remotely from the mammography unit 12. In the illustrated embodiment, the connector box 24 and the umbilical cable 22 include a plurality of conductors for transmitting electrical signals and at least one optical fiber for transmitting optical energy.

In the illustrated embodiment, the connector box 24 includes a plurality of sockets 26 and 28 and at least one fiber optic cable connector 30. The sockets 26 and 28 are labeled Energy Probe and Sensing Probe, respectively. In an alternative embodiment, the connector box includes two or more fiber optic cable connectors such as connector 30, and the umbilical cable includes at least two optical fibers for connecting the connectors such as connector 30 to a plurality of energy sources configured to emit optical energy located remotely from the mammography unit 12.

Figure 4:
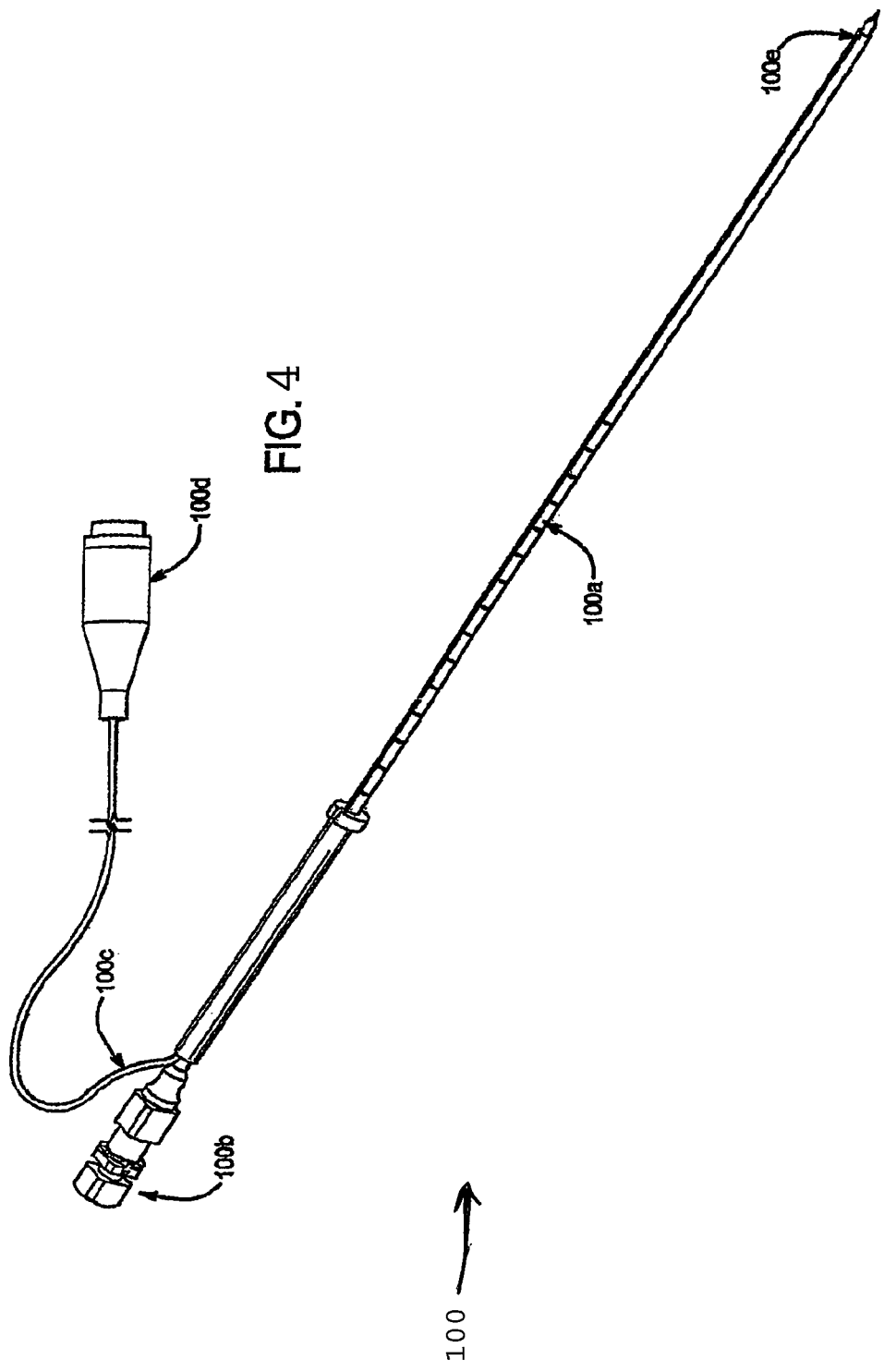
FIG. 4 is a fragmentary perspective view of one embodiment of the energy probe disclosed herein.

Referring now to FIG. 4, an example embodiment of the energy probe 100 is illustrated. In the illustrated embodiment, the energy probe 100 includes a hollow cannula 100a. The energy probe also includes a stylet 100b configured to be removably insertable in the cannula 100a. In one embodiment, when the stylet is inserted in the cannula, the energy probe enables an opening to be formed in the skin by puncturing the skin such that the tip of probe is positionable percutaneously in the tumor mass.

The energy probe 100 also includes at least one sensor 100e. In the illustrated embodiment, the sensor 100e is connected to an energy probe connector 100d by way of a sensor wire 100c. In one embodiment, the sensor is a thermistor and is configured to detect a resistance and to send an electrical signal to the energy probe connector 100d indicative of a detected temperature at the tip of the energy probe 100. In another embodiment, the sensor 100e is a dosimeter configured to measure a dosage amount at the tip of the energy probe 100. In various embodiments, the energy probe includes a plurality of sensors such as sensor 100e for measuring temperature and dosage at the tip of the energy probe. It should be appreciated that in these embodiments, the electronic signals indicating a detected temperature and/or dosage for each of the sensors such as sensor 100e travel through the sensor wire 100c and into the connector 100d.

The energy probe is configured to be insertable through at least one probe holder, as discussed in detail below. The energy probe is also configured such that when the stylet 100b is removed from the cannula 100a, at least one optical fiber is insertable in the energy probe 100. In various embodiments, the cannula 100a of the probe 100 is further configured to enable an optical fiber and a volume of liquid to be positioned in the probe. In various embodiments, the liquid is saline and functions as a heat-transfer medium, as discussed below.

As discussed above, in the embodiment of the energy probe 100 illustrated in FIG. 4, the diameter of the energy probe 100 is substantially constant throughout the length of the energy probe 100. Moreover, as discussed above with respect to FIG. 1, the diameter of the energy probe 100 in various embodiments is relatively small compared with the diameter of a tumor mass to be treated. Thus, it should be appreciated that the energy probe 100 illustrated in FIGS. 1 and 4 is not configured to maintain a cavity approximating the size of the tumor mass during application of therapeutic energy as described herein.

Figure 5:
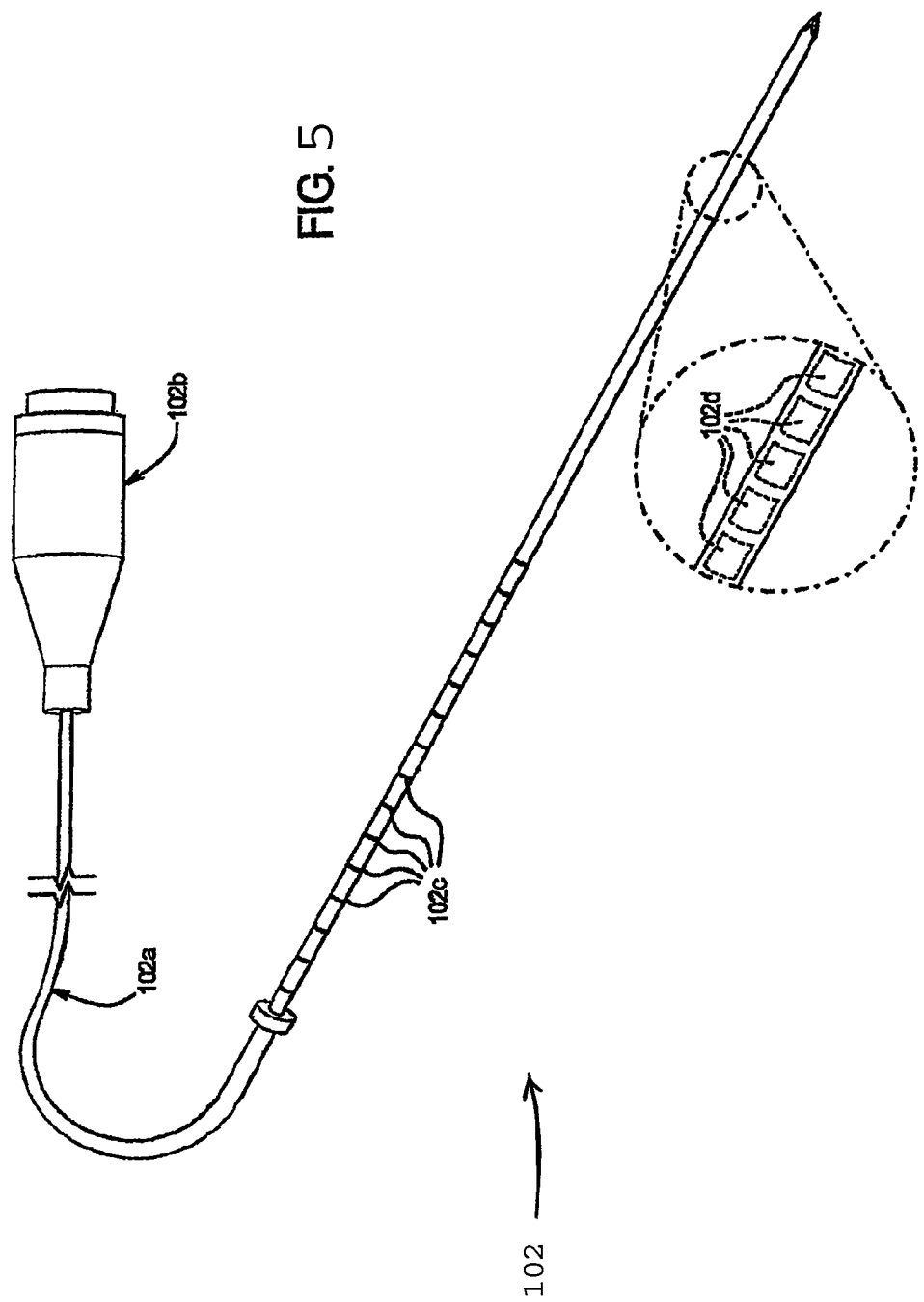
FIG. 5 is a fragmentary perspective view of one embodiment of the sensing probe disclosed herein.

FIG. 5 illustrates an example embodiment of the sensing probe 102 disclosed herein. The sensing probe 102 includes a sensor wire 102a which his configured to send electrical signals representing a plurality of conditions sensed by the sensing probe to a connector 102b. The sensing probe 102 also includes a plurality of evenly spaced-apart marks 102c for positioning the sensing probe with respect to the energy probe, as discussed below.

The sensing probe further includes a plurality of sensors 102d. In one embodiment, the sensors 102d are thermistors configured to sense a plurality of resistances. In this embodiment, each thermistor 102d is connected by a conductor (not shown) to the sensing probe wire 102a, which in turn communicates the signals indicative of detected resistances to the connector 102b.

In another embodiment, the sensors 102d are a plurality of dosimeters configured to measure a plurality of charge differences between two electrodes. In this embodiment, each of the sensors 102d is connected by an appropriate conductor to the sensor wire 102a. The conductors are configured to send electronic signals indicative of a plurality of charge differences to the connector 102b. In various embodiments, the conductors are also configured to deliver electrical charge to two electrodes of each dosimeter 102d to maintain any required charge difference between the electrodes.

In various embodiments, the sensors 102d include a plurality of thermistors for measuring a plurality of temperatures and a plurality of dosimeters for measuring a plurality of dosage amounts. In this embodiment, it should be appreciated that a single sensing probe enables an operator to determine the amount of energy applied to a tumor based on the temperature of tissue adjacent to the tumor and based on the dosage amount received by tissue adjacent to the tumor. Thus, a sensing probe 102 including at least one dosimeter and at least one thermistor enables an operator to perform both interstitial laser therapy and brachytherapy.

The sensing probe is configured to be insertable in at least one probe holder, as discussed below. In this embodiment, the sensing probe is further configured to be positioned with respect to the energy probe based on the plurality of evenly spaced-apart marks 102c of the sensing probe. The sensing probe is also configured to include a trocar or other appropriate structure on the tip of the probe such that pressure applied to the sensing probe enables the sensing probe to puncture the skin such that the plurality of sensors 102e are positionable adjacent to a percutaneous tumor.

In an alternative embodiment, the therapeutic system disclosed herein includes at least two sensing probes such as sensing probe 102 wherein at least one sensing probe is a thermal probe and wherein at least one sensing probe is a dosage probe. In this embodiment, the at least one thermal probe includes one or more thermistors for measuring one or more temperatures of tissue adjacent to the tissue of interest, and the at least one dosage probe includes one or more dosimeters for measuring one or more dosage amounts of tissue adjacent to the tissue of interest.

Figure 6:
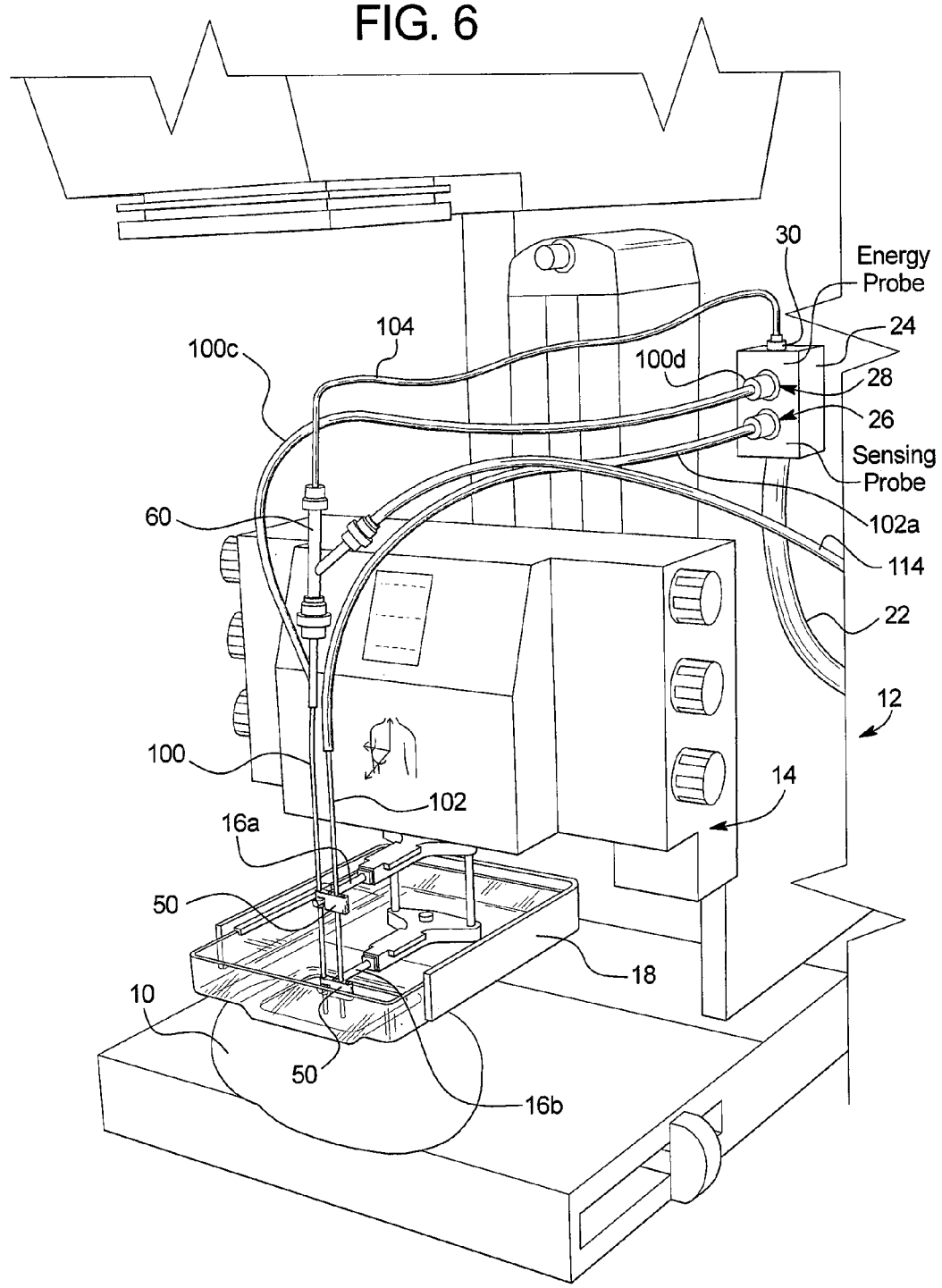
FIG. 6 is a fragmentary perspective view of the apparatus for performing interstitial laser therapy and brachytherapy, including the components in the two disclosed categories configured to perform interstitial laser therapy.

FIG. 6 illustrates an example embodiment of the components of category one combined with the components of category two. It should be appreciated that FIG. 6 does not illustrate the plurality of energy sources, the plurality of sensor controllers, or the computer. In the illustrated embodiment, the umbilical cable 22 and the connector box enable the illustrated components illustrated to co-act with the plurality of energy sources, the plurality of sensor controllers, and the computer.

In the illustrated embodiment, the energy probe 100 is positioned in the tumor mass 10 (which, as noted above, is illustrated as a saline bag). The probe holders 50 are configured to be rotatably insertable in the probe holder attachments 16a and 16b. In the illustrated embodiment, two probe holders 50 thus position the energy probe with respect to the tumor mass 10. In the illustrated embodiment, the energy probe 100 includes at least one thermistor and at least one dosimeter positioned near the tip of the energy probe. The energy probe wire 100c is configured to be connectable to the umbilical box such that a plurality of conductors within the energy probe wire 100c enable electrical signals to be sent from the at least one dosimeter and the at least one thermistor to the connector box 24. As illustrated, the energy probe wire 100c is connected to the connector box 24 by way of the energy probe socket 26. It should be appreciated that at least one wire of the umbilical cable 22 is configured to further send these electrical signals to the appropriate energy controller 240 or 250.

The probe holders 50 are further configured to position the sensing probe 102 with respect to the tumor mass 10. In the illustrated embodiment, the sensing probe 102 includes a plurality of thermistors and a plurality of dosimeters 102d (not shown) mounted near the end of the sensing probe inserted in the tissue adjacent to the tumor mass. Moreover, the sensing probe 102 includes a sensing probe wire 102a which includes a plurality of conductors for sending electrical signals indicating a plurality of temperatures or a plurality of dosage amounts to the connector box 24. In the illustrated embodiment, a single wire 102a includes each of the conductors for sending a signal from each dosimeter and each thermistor. As illustrated, the sensing probe wire 102a is configured to be connected to the connector box 24 by way of sensing probe socket 28. It should be appreciated that at least one wire of the umbilical cable 22 is configured send these electrical signals to the appropriate energy controller 240 or 250.

The configuration of the components of the disclosed therapeutic system illustrated in FIG. 6 enables an operator to perform interstitial laser therapy. In this embodiment, a hemostasis valve 60 is removably connected to the energy probe 100. The hemostasis value 60 includes three ports. One of the ports is connected to the energy probe, and one of the ports enables a flow of a liquid to act as a heat transfer medium, such as saline, and one of the ports enables a laser optical fiber 104 to be inserted through the hemostasis valve 60 and into the energy probe 100. In the illustrated embodiment, saline is provided to the energy probe 100 by way of saline tube 114. In the illustrated embodiment, the laser optical fiber 104 is positioned in the hemostasis valve and further in the energy probe 100 such that the tip of the laser optical fiber 104 is even with the tip of the energy probe 100. Moreover, the laser optical fiber 104 is connected to the connector box 24 by way of the optical fiber connector 30.

It should be further appreciated that the disclosed therapeutic system, illustrated in FIG. 6, enables an operator to easily and quickly switch from performing interstitial laser therapy to performing brachytherapy. In the illustrated embodiment, to switch from performing interstitial laser therapy to performing brachytherapy, the operator removes the laser optical fiber 104 and the hemostasis valve 60 from the energy probe 100. The operator also disconnects the laser optical fiber 104 from the connector box 24. To perform brachytherapy, the operator connects the x-ray optical fiber 105 to the connector box 24 and inserts the x-ray optical fiber 105 in the energy probe 100. The operator finally makes any necessary changes with respect to the x-ray energy source 150 (such as changing a connector from the umbilical cable 22 from the laser energy source 140 to the x-ray energy source 150). After the operator has performed the above actions, the disclosed therapeutic system is configured to perform brachytherapy by applying x-ray energy to the tumor.

Figure 7A:
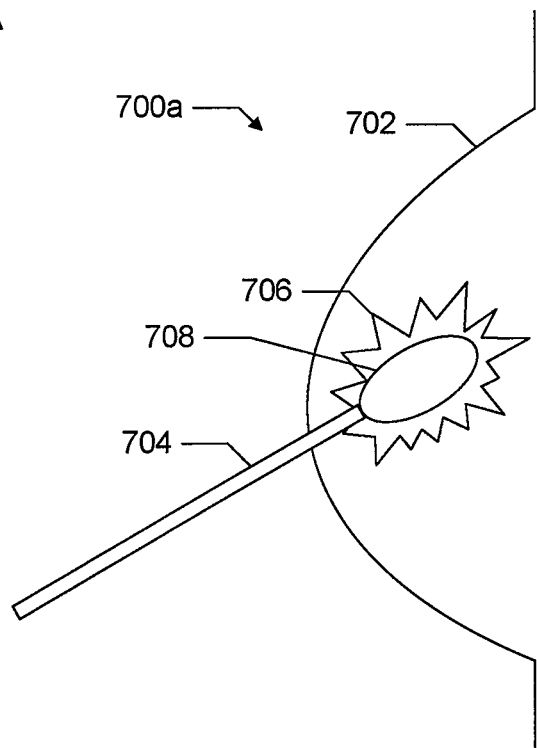
FIG. 7A is a schematic diagram of a conventional balloon catheter-based brachytherapy apparatus.

FIG. 7A is a schematic diagram 700a of a conventional balloon catheter-based brachytherapy apparatus. FIG. 7A illustrates a schematic view of a body part to be treated in the form of breast 702. In the illustrated embodiment, a cavity 706 has been previously formed by an operator performing a surgical procedure, such as a lumpectomy, as is known in the art. A catheter 704 is inserted into the body part to be treated 702 and into the cavity 706. In the illustrated embodiment, in order to ensure accurate delivery of therapeutic energy (i.e., x-ray energy), the apparatus of FIG. 7A, includes a balloon 708 or other appropriate structure to ensure that the cavity 706 remains uniform and does not collapse during treatment. In a further embodiment, conventional brachytherapy apparatus such as those illustrated in FIG. 7A require that the balloon 708 be inflated until the cavity 706 attains a spherical or substantially spherical shape. Thus, it should be appreciated that conventional apparatus such as the apparatus illustrated in FIG. 7A require a balloon 708 or other device to ensure the integrity and uniformity of the cavity 706 during therapy.

Figure 7B:
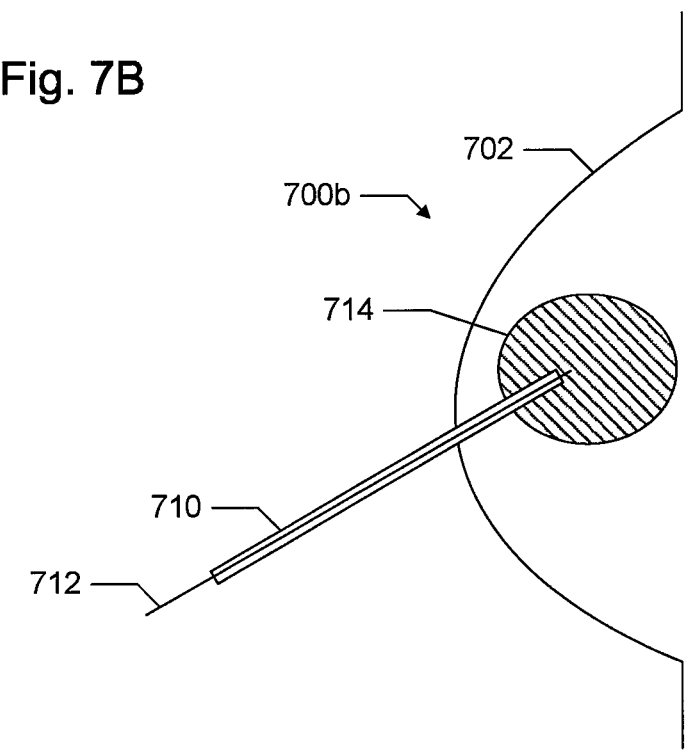
FIG. 7B is a schematic diagram of a brachytherapy apparatus, which does not operate in a cavity and thus does not require a balloon or other device to maintain the cavity, as disclosed herein.

FIG. 7B is a schematic diagram 700b of an embodiment of the disclosed brachytherapy apparatus, which does not operate in a cavity and thus does not require a balloon or other device to maintain the cavity. In the embodiment illustrated in FIG. 7B, the body part to be treated remains the breast 702. In the illustrated embodiment, however, no cavity has been created during a treatment preceding brachytherapy, such as during the interstitial laser therapy treatment described herein. Thus, the zone of treatment 714 for brachytherapy does not include a cavity, but rather includes substantially uniform tissue mass, illustrated as a cross-hatched area of tissue mass, which will not collapse or otherwise deform during treatment. Since tissue mass 714 does not include a cavity, the apparatus disclosed herein does not require a balloon or other device to maintain a cavity during brachytherapy. Thus, the illustrated embodiment of the disclosed apparatus includes a probe 710 with a fiber 712 inserted therethrough, wherein the tip of the probe/fiber combination is approximately centered in the tissue mass 714. During brachytherapy performed using the illustrated embodiment of the disclosed apparatus, an operator applies x-ray energy to the fiber 712, which energy is directed into the tissue mass 714, and therapeutically applied to the breast 702. Moreover, due to the physical properties of tissue to be treated, the energy delivered during brachytherapy will be delivered in a substantially spherical pattern—a result which could only be achieved in the prior art by using a balloon or other similar device to force a cavity into a spherical shape.

It should thus be appreciated that because the disclosed brachytherapy treatment and apparatus is utilized in conjunction with interstitial laser therapy as described herein, no balloon or other device is needed to maintain the integrity of any cavity—indeed, no cavity is formed during the interstitial laser therapy. Thus, the disclosed apparatus enables delivery of uniform x-ray or other therapeutic energy during a brachytherapy treatment using a substantially simplified device and immediately following another therapy, such as interstitial laser therapy. It should be further appreciated that the apparatus disclosed herein is not limited to the apparatus illustrated in FIG. 7B—rather, the apparatus of FIG. 7B is merely exemplary. For example, instead of directing x-ray or other therapeutic energy into the tissue mass 714 using a fiber 712, the disclosed apparatus could utilize one or more brachytherapy seeds or other energy sources to generate and direct such energy.

It should be appreciated that the present disclosure is not limited to a therapeutic system for performing interstitial laser energy therapy and brachytherapy, and particularly, is not limited to a therapeutic system for applying laser energy and x-ray energy to a tumor mass in a breast. The present disclosure may apply to a variety of different non-surgical treatments for the destruction of a variety of different tumor masses.

In various embodiments, certain components of the system disclosed herein are usable to deliver various combinations of x-ray energy, laser energy, and other types of therapeutic energy to tissue to be treated during a single treatment. In one embodiment, the single treatment includes delivery of therapeutic energy, but does not include further removal of tissue to be treated. In another embodiment, the system disclosed herein is usable in conjunction with, in combination with, or coincident to known procedures for surgical excision of tissue to enhance the results of a single treatment. In an example embodiment, certain components of the disclosed system are usable coincident to a known lumpectomy procedure to treat tissue and to enhance the results obtained from such treatment. In other embodiments, the components of the system disclosed herein are usable to perform other types of surgical excision of tissue known to one of ordinary skill in the art.

It should be understood that modifications and variations may be effected without departing from the scope of the novel concepts of the present disclosure, and it should be understood that this application is to be limited only by the scope of the appended claims.

The invention is claimed as follows:

1. A therapeutic energy application system comprising:
   a laser energy source;
   an x-ray energy source;
   an energy probe insertable into a tissue at a first position;
   a stylet removably insertable into the energy probe, wherein the stylet is in the energy probe when the energy probe is inserted into the tissue, and wherein the stylet is configured to be removed from the energy probe after the energy probe is inserted into the tissue at the first position;
   a laser optical fiber configured to be connectable to the laser energy source, the laser optical fiber removably insertable into the energy probe after the stylet is removed from the energy probe, and configured to emit laser energy to heat and ablate tissue;
   an x-ray optical fiber configured to be connectable to the x-ray energy source, the x-ray optical fiber removably insertable into the energy probe after the stylet is removed from the energy probe and when the laser optical fiber is not in the energy probe;
   a sensing probe separate from the energy probe, the sensing probe configured to be independently and separately inserted into the tissue at a second position spaced apart from the first position and configured to detect at least one temperature; and
   at least one microprocessor configured to co-act with the laser energy source, the x-ray energy source, and the at least one sensing probe to:
      send a signal to the laser energy source to change the amount of laser energy generated,
      receive a signal from the at least one sensing probe indicating a detected temperature, and
      send a signal the x-ray energy source to change the amount of x-ray energy generated.

2. The therapeutic energy application system of claim 1, including at least one display device configured to co-act with the at least one microprocessor to display a graphical representation of the signal from the sensing probe indicating a detected temperature.

3. The therapeutic energy application system of claim 1, including at least one input device configured to co-act with the at least one microprocessor to enable an operator to cause the at least one microprocessor to send a signal to the laser energy source to change the amount of laser energy emitted.

4. The therapeutic energy application system of claim 1, including at least one storage device configured to co-act with the at least one microprocessor to store the signal from the sensing probe indicating a detected temperature.

5. The therapeutic energy application system of claim 1, including at least one input device configured to co-act with the at least one microprocessor to enable an operator to cause the at least one microprocessor to send a signal to the x-ray energy source to change the amount of x-ray energy emitted.

6. The therapeutic energy application system of claim 1, wherein the microprocessor is further configured to co-act with the laser energy source, the x-ray energy source, and the sensing probe, to send a signal to at least one of the laser energy source and the x-ray energy source to cause at least one of the laser energy source and the x-ray energy source to stop emitting energy.

7. The therapeutic energy application system of claim 1, wherein the at least one energy probe includes a substantially constant diameter along the energy probe, such that the energy probe does not maintain a cavity during an application of therapeutic energy.

8. The therapeutic energy application system of claim 7, which does not include a balloon.

9. The therapeutic energy application system of claim 1, wherein a surgical excision of tissue is performed coincident to the at least one microprocessor co-acting with the laser energy source, the x-ray energy source, and the sensing probe.

10. The therapeutic energy application system of claim 1, wherein the sensing probe is configured to detect at least one dosage amount.

11. The therapeutic energy application system of claim 10, including at least one display device configured to co-act with the at least one microprocessor to display a graphical representation of the signal from the sensing probe indicating a detected temperature and to display a graphical representation of the signal from the sensing probe indicating a detected dosage amount.

12. The therapeutic energy application system of claim 10, including at least one storage device configured to co-act with the at least one microprocessor to store the signal from the sensing probe indicating a detected temperature and to store the signal from the sensing probe indicating a detected dosage amount.

* * * * *

UNITED STATES PATENT AND TRADEMARK OFFICE
CERTIFICATE OF CORRECTION

| | | |
|---|---|---|
| PATENT NO. | : 8,663,210 B2 | Page 1 of 1 |
| APPLICATION NO. | : 12/778580 | |
| DATED | : March 4, 2014 | |
| INVENTOR(S) | : Tomasello | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 378 days.

Signed and Sealed this
Second Day of June, 2015

Michelle K. Lee
*Director of the United States Patent and Trademark Office*